US007700283B2

(12) United States Patent
Evans et al.

(10) Patent No.: US 7,700,283 B2
(45) Date of Patent: Apr. 20, 2010

(54) REPAIR OF NUCLEIC ACIDS FOR IMPROVED AMPLIFICATION

(75) Inventors: Thomas C. Evans, Topsfield, MA (US); Barton Slatko, Ipswich, MA (US); Lixin Chen, Beverly, MA (US); Romaldas Vaisvila, Ipswich, MA (US); Chudi Guan, Wenham, MA (US)

(73) Assignee: New England Biolabs, Inc., Ipswich, MA (US)

( * ) Notice: Subject to any disclaimer, the term of this patent is extended or adjusted under 35 U.S.C. 154(b) by 214 days.

(21) Appl. No.: 11/255,290

(22) Filed: Oct. 20, 2005

(65) Prior Publication Data

US 2006/0088868 A1   Apr. 27, 2006

Related U.S. Application Data

(60) Provisional application No. 60/620,896, filed on Oct. 21, 2004, provisional application No. 60/646,728, filed on Jan. 24, 2005, provisional application No. 60/673,925, filed on Apr. 21, 2005.

(51) Int. Cl.
 *C12Q 1/68* (2006.01)

(52) U.S. Cl. .......................... 435/6; 435/91.1; 435/91.2

(58) Field of Classification Search ........................ None
See application file for complete search history.

(56) References Cited

U.S. PATENT DOCUMENTS

| | | | |
|---|---|---|---|
| 5,035,996 A | 7/1991 | Hartley | |
| 5,455,166 A | 10/1995 | Walker | |
| 5,459,039 A | 10/1995 | Modrich et al. | |
| 5,470,723 A | 11/1995 | Walker et al. | |
| 6,060,288 A * | 5/2000 | Adams et al. | 435/91.2 |
| 6,872,552 B2 * | 3/2005 | Ensley | 435/91.2 |
| 7,217,514 B2 * | 5/2007 | Padgett et al. | 435/6 |
| 2003/0077581 A1 | 4/2003 | Ensley | |
| 2003/0119150 A1 | 6/2003 | Ankenbauer et al. | |
| 2004/0058378 A1 | 3/2004 | Kong et al. | |
| 2004/0067559 A1 | 4/2004 | McCarthy et al. | |
| 2005/0026147 A1 * | 2/2005 | Walker et al. | 435/6 |
| 2005/0069991 A1 * | 3/2005 | Hyman | 435/91.2 |
| 2005/0196392 A1 * | 9/2005 | Andersen | 424/94.61 |
| 2006/0014154 A1 * | 1/2006 | Eshoo | 435/6 |
| 2006/0115838 A1 * | 6/2006 | Bazar et al. | 435/6 |

FOREIGN PATENT DOCUMENTS

| | | |
|---|---|---|
| WO | WO 0151656 | 7/2001 |
| WO | WO 2005017173 | 2/2005 |

OTHER PUBLICATIONS

Nicholl et al., "Reconstitution of Human Base Excision Repair with Purified Proteins," Biochemistry, 1997, vol. 36, pp. 7557-7566.*
Dianov, et al., "Reconstitution of the DNA base excision-repair pathway," Current Biology, 1994, vol. 4, No. 12, pp. 1069-1076.*
Barany. PNAS vol. 88:189-193. 1991.*
Barnes, et al., *Gene* 112:29-35 (1992).
Barnes, W. M., *Proc. Natl. Acad. Sci. USA* 91:2216-2220 (1994).
Bowater, R. P., et. al., *Biochemistry* 33:9266-9275 (1994).
Bucklin, A. & Allen, L. D., *Mol. Phylogenet. Evol.* 30(3):879-882 (2004).
Costa et al., *Biochimie* 85(11):1083-1099 (2003).
Di Benardo et al., *Nucl. Acids Res.* 30(4):e16 (2002).
Eisen, J.A. and Hanawalt, P.C., *Mutat. Res.* 435(3):171-213 (1999).
Fire and Xu, *Proc. Natl. Acad Sci. USA* 92:4641-4645 (1995).
Fromenty, B., et al., *Nucl. Acids Res.* 28(11):e50 (2000).
Ghadessy et al., *Nature Biotechnol.* 22(6):755-9 (2004).
Gilbert, et al., *Am. J. Hum. Gen.* 72:48-61 (2003).
Guan, C., et.al., *Biochemistry* 43:4313-4322 (2004).
Guatelli et al., *Proc. Natl. Acad. Sci. USA* 87:1874-1878 (1990).
Hofreiter et al., *Nucl. Acids Res.* 29:4793-9 (2001).
Ide, H., et al., *Biochemistry* 32(32):8276-83 (1993).
Kayser,K, *Origins Sigma-Aldrich* 14:4-5 (2004).
Kermekchiev, M. B. et al., *Nucl. Acids Res.* 31:6139-47 (2003).
Lizardi, et al., *Nature Genetics* 19:225-232 (1998).
Liu, et al., *J. Am. Chem. Soc.* 118:1587-1594 (1996).
Liu, Y., et al., *Annu. Rev. Biochem.* 73:589-615 (2004).
Lowell, J. L. & Klein, D. A., *Biotechniques* 28:676-681 (2000).
Minko et al., *Biochemistry* 44:3000-3009 (2005).
Moolenar et al., *Proc. Natl Acad Sci USA* 99:1467-72 (2002).
Parkinson, M. J. & Lilley, D. M., *J. Mol. Biol.* 270:169-178 (1997).
Pusch, et al., *Nucl. Acids Res.* 26:857 (1998).
Eds. Sambrook and Russell, Molecular Cloning: A Laboratory Manual, 3$^{rd}$ ed., Cold Spring Harbor Press, Cold Spring Harbor, NY, 2001, Chs. 1,5,8,11,12,15 pp. 6.25, A8.12-A8.24.
Sancar, *Ann. Rev. Biochem* 65:43-81 (1996).
Sattler, et al., *Arch. Biochem Biophys.* 376(1):26-3 (2000).
Smith, J. & Modrich, P., *Proc. Natl. Acad. Sci. USA* 94:6847-6850 (1997).
Thompson, J. R., et al., *Nucl. Acids Res.* 30(9):2083-2088 (2002).
Vande Berg, et al., *J. Biol. Chem.* 273(32):20276-20284 (1998).
Wellinger, et al., *Nucleic Acids Res.* 24(8):1578-79 (1996).
Wood, R.D., et al., *Mutat. Res.* 577(1-2):275-83 (2005).
Xu, Y., et al. J., *Biol. Chem.* 275(27):20949-20955 (2000).
Zou, Y., et al., *Biochemistry* 43:4196-4205 (2004).

* cited by examiner

*Primary Examiner*—Heather G Calamita
(74) *Attorney, Agent, or Firm*—Harriet M. Strimpel

(57) ABSTRACT

Methods and compositions are provided for repairing a polynucleotide so that it can be synthesized efficiently with improved fidelity and yield in, for example, an amplification reaction. This involves the use of a reaction mixture that includes a ligase and a cofactor selected from NAD+ or ATP and incubating the polynucleotide with the reaction mixture in the absence of Endonuclease VI.

The reaction mixture may further contain an AP endonuclease and a polymerase. These enzymes are optionally selected according to their ability to withstand high temperatures so they can be included in an amplification mixture. The reaction mixture may be used prior to a polynucleotide synthesis reaction in which case enzymes that are not thermophilic may be used. The repair reaction is not time sensitive with respect to seconds, minutes or hours of incubation in the enzyme mixture.

27 Claims, 19 Drawing Sheets

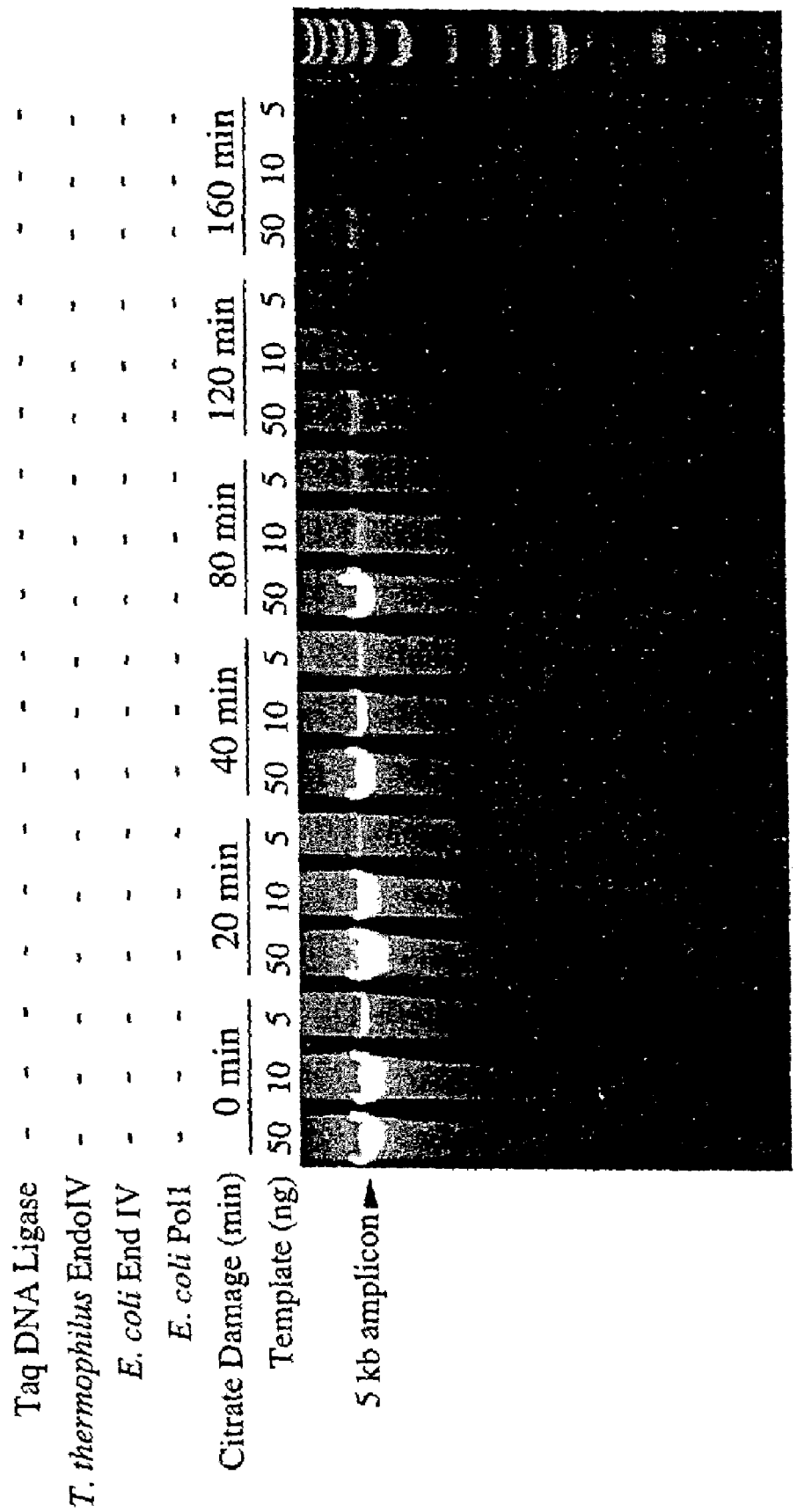

Figure 6-1

```
_  5   38   88 1092  >gi|2258283|gb|AAB63574.1| replication factor
C like protein [Emericella nidulans]
+  5   38   88 1092  >gi|2773537|gb|AAB63523.2| replication factor
C like protein [Emericella nidulans]
+  5   38   88 1092  >gi|40739497|gb|EAA58687.1| hypothetical
protein AN6303.2 [Aspergillus nidulans FGSC A4]
+  5   38   88 1092  >gi|49097960|ref|XP_410440.1| hypothetical
protein AN6303.2 [Aspergillus nidulans FGSC A4]
+  5   38   88 1092  >gi|7493935|pir||T18305 replication factor C
like protein - Emericella nidulans
+  5   38   88 1092  >gi|7493936|pir||T18306 replication factor C
protein - Emericella nidulans
_  5   63  166  623  >gi|48141611|ref|XP_397246.1| similar to
Activator 1 140 kDa subunit (Replication factor C large subunit)
(Germline transcription factor 1) [Apis mellifera]
_  5   63  173 1051  >gi|31242853|ref|XP_321857.1|
ENSANGP00000020306 [Anopheles gambiae]
_  5   75  214  952  >gi|49646861|emb|CAG83248.1| unnamed protein
product [Yarrowia lipolytica CLIB99]
_  5   75  214  952  >gi|50547051|ref|XP_500995.1| hypothetical
protein [Yarrowia lipolytica]
_  5   78  233  603  >gi|55234052|gb|EAA01207.3| ENSANGP00000020306
[Anopheles gambiae str. PEST]
_  5  102  307 1147  >gi|2827257|gb|AAB99788.1| DNA binding protein
[Homo sapiens]
+  5  102  307 1147  >gi|296908|emb|CAA80355.1| PO-GA [Homo sapiens]
+  5  102  307 1147  >gi|30354564|gb|AAH51751.1| Replication factor
C large subunit [Homo sapiens]
_  5  102  307 1147  >gi|32528306|ref|NP_002904.3| replication
factor C large subunit [Homo sapiens]
+  5  102  307 1147  >gi|422807|pir||JN0599 DNA-binding protein PO-GA
human
+  5  102  307 1147  >gi|46430941|gb|AAS94325.1| replication factor
C (activator 1) 1, 145kDa [Homo sapiens]
+  5  102  307 1147  >gi|53972062|gb|AAV20814.1| Sequence 1074 from
patent US 6753314
_  5  102  307 1148  >gi|2136100|pir||A49651 replication factor C
large subunit - human
_  5  102  307 1148  >gi|30353858|gb|AAH51786.1| RFC1 protein [Homo
sapiens]
+  5  102  307 1148  >gi|410218|gb|AAA16121.1| replication factor C
large subunit
_  5  102  307 1148  >gi|52632416|gb|AAH35297.1| Replication factor
C large subunit [Homo sapiens]
```

Figure 6-2

```
_   5  102  307  1148  >gi|56757608|sp|P35251|RFC1_HUMAN Activator 1
140 kDa subunit (Replication factor C large subunit) (A1 140 kDa
subunit) (RF-C 140 kDa subunit) (Activator 1 large subunit)
(DNA-binding protein PO-GA)
_   5  102  357   748  >gi|14591755|ref|NP_143722.1| ERCC4-like
helicase/ERCC4-type nuclease [Pyrococcus horikoshii OT3]
_   5  125  416  1001  >gi|50255468|gb|EAL18203.1| hypothetical
protein CNBK2210 [Cryptococcus neoformans var. neoformans B-3501A]
_   5  153  672   636  >gi|55416925|gb|AAV50575.1| NAD-dependent DNA
ligase [Mimivirus]
_   5  153  672   636  >gi|55819181|ref|YP_142657.1| NAD-dependent
DNA ligase [Mimivirus]
_   5  159  540   656  >gi|48837044|ref|ZP_00294039.1| COG0322:
Nuclease subunit of the excinuclease complex [Thermobifida fusca]
_   5  162  568  1084  >gi|38105148|gb|EAA51609.1| hypothetical
protein MG03204.4 [Magnaporthe grisea 70-15]
+   5  162  568  1084  >gi|39942248|ref|XP_360661.1| hypothetical
protein MG03204.4 [Magnaporthe grisea 70-15]
_   5  185  653   679  >gi|50875895|emb|CAG35735.1| related to
NAD-dependent DNA ligase [Desulfotalea psychrophila LSv54]
+   5  185  653   679  >gi|51244858|ref|YP_064742.1| related to
NAD-dependent DNA ligase [Desulfotalea psychrophila LSv54]
_   5  192  735   860  >gi|49654048|emb|CAG86464.1| unnamed protein
product [Debaryomyces hansenii CBS767]
+   5  192  735   860  >gi|50419709|ref|XP_458382.1| unnamed protein
product [Debaryomyces hansenii]
_   5  220  688   679  >gi|14089803|emb|CAC13562.1| DNA LIGASE
(POLYDEOXYRIBONUCLEOTIDE SYNTHASE [NAD+]) [Mycoplasma pulmonis]
_   5  220  688   679  >gi|15828860|ref|NP_326220.1| DNA LIGASE
(POLYDEOXYRIBONUCLEOTIDE SYNTHASE [NAD+]) [Mycoplasma pulmonis UAB
CTIP]
+   5  220  688   679  >gi|25293995|pir||E90560 hypothetical protein
MYPU_3890 [imported] - Mycoplasma pulmonis (strain UAB CTIP)
_   5  226  749   823  >gi|15639622|ref|NP_219072.1| DNA ligase (lig)
[Treponema pallidum subsp. pallidum str. Nichols]
+   5  226  749   823  >gi|3322933|gb|AAC65609.1| DNA ligase (lig)
[Treponema pallidum subsp. pallidum str. Nichols]
_   5  226  749   823  >gi|6014987|sp|O83642|DNLJ_TREPA DNA ligase
(Polydeoxyribonucleotide synthase [NAD+])
_   5  226  749   823  >gi|7521016|pir||H71300 probable DNA ligase
(lig) - syphilis spirochete
_   5  230  678   660  >gi|15594897|ref|NP_212686.1| DNA ligase (lig)
```

Figure 6-3

[Borrelia burgdorferi B31]
+    5  230  678  660  >gi|2688477|gb|AAC66923.1| DNA ligase (lig)
[Borrelia burgdorferi B31]
+    5  230  678  660  >gi|7428521|pir||G70168 DNA ligase (NAD) (EC
6.5.1.2) - Lyme disease spirochete
_    5  230  678  660  >gi|7673988|sp|O51502|DNLJ_BORBU DNA ligase
(Polydeoxyribonucleotide synthase [NAD+])
_    5  236  938  867  >gi|2837635|gb|AAC41087.1| major surface
protein 3 [Anaplasma marginale]
_    5  457  1834  984  >gi|14325803|gb|AAK60014.1| topoisomerase V
[Methanopyrus kandleri]
_    5  457  1834  984  >gi|19888102|gb|AAM02649.1| Topoisomerase V
[Methanopyrus kandleri AV19]
_    5  457  1834  984  >gi|20094872|ref|NP_614719.1| Topoisomerase V
[Methanopyrus kandleri AV19]

Figure 7 (SEQ ID NO:11)

```
atgccgcgct acgggttcca cctttccatc gccgggaaaa agggcgtggc
cggggcggtg gaggaggcca ccgccctcgg cctcaccgct ttccagatct
tcgccaaaag cccgcggagc tggcgcccaa gggccctctc cccggccgag
gtggaggcct tccgcgcctt aagggaggcc tccggggcc tccccgccgt
gatccacgcc tcctacctgg tcaacctggg ggcggagggg gagctttggg
agaagagcgt ggcgagcctg gcggacgacc tggagaaggc cgccctcctc
ggggtggagt acgtggtcgt ccacccggc tgggccgcc ccgagcgggt
caaggaaggg gccctcaagg ccctgcgcct cgccggcgtc cgctcccgcc
ccgtcctcct cgtggagaac accgccgggg gcggggagaa ggtgggggcg
cggtttgagg agctcgcctg gctcgtggcg gacaccccc tccaggtctg
cctggacacc tgccacgcct acgccgccgg gtacgacgtg gccgaggacc
ccttgggggt cctggacgcc ctgaccgggg ccgtgggcct ggagcgggtg
cccgtggtcc acctcaacga ctccgtgggc ggcctcggaa gccgcgtgga
ccaccacgcc cacctcctcc agggaaagat cggggagggg ctcaagcgcg
tcttcttgga cccgaggctc aaggaccggg tcttcatcct ggaaaccccc
aggggaccgg aggaggacgc ctggaacctc cgggtcctca gggcctggct
cgaggaggcc taa
```

Figure 9
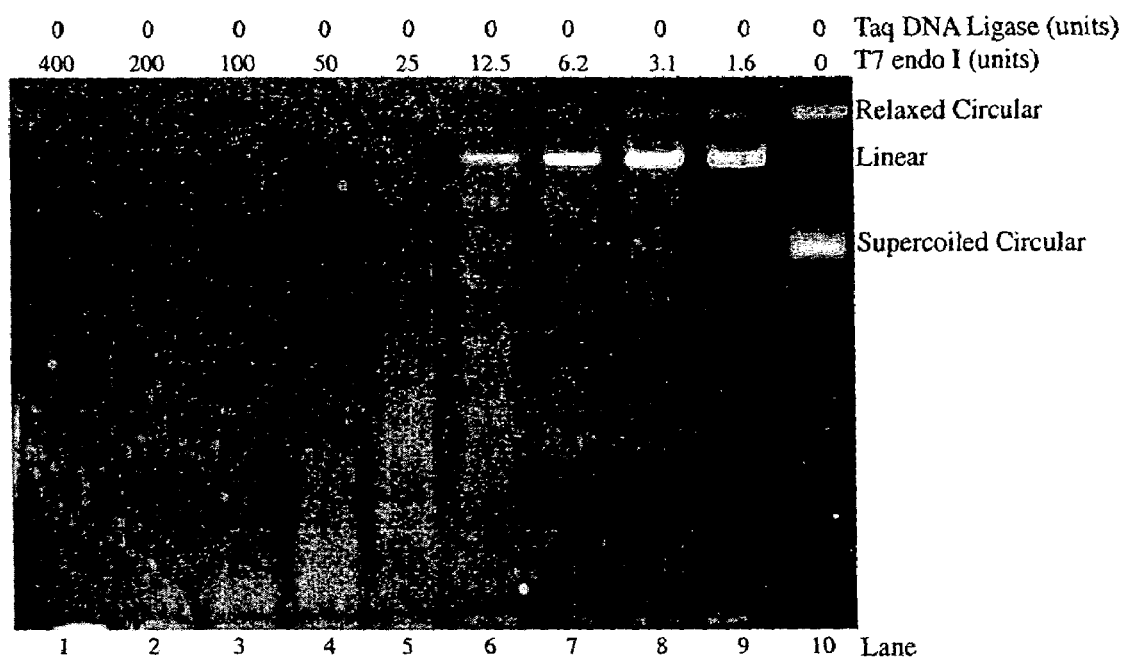
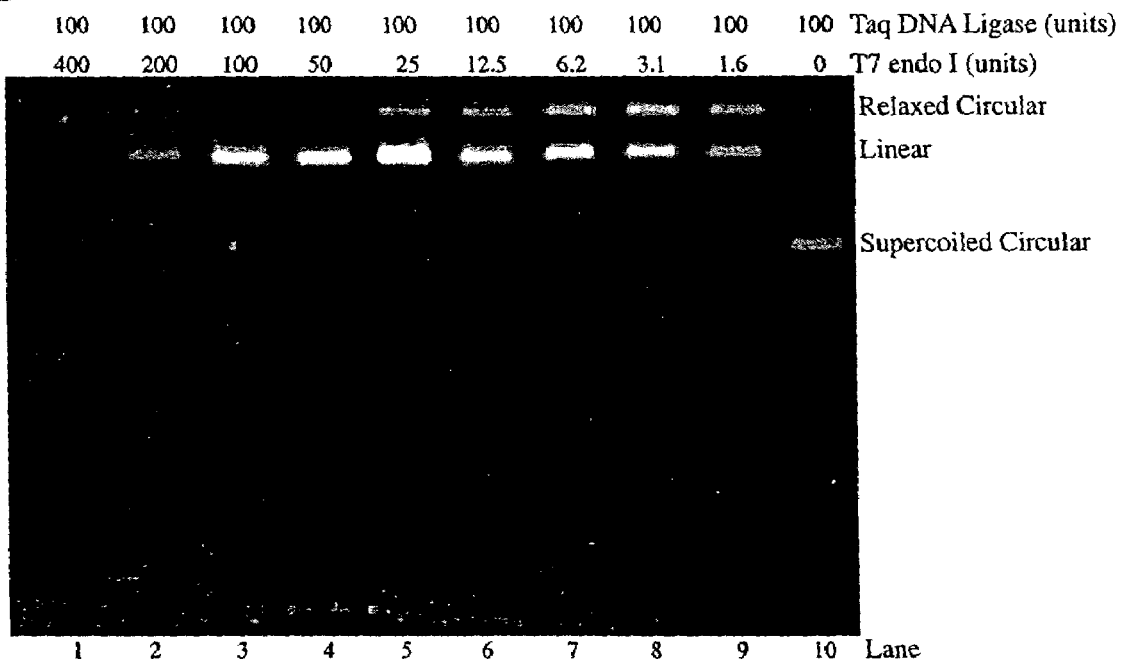

Figure 10
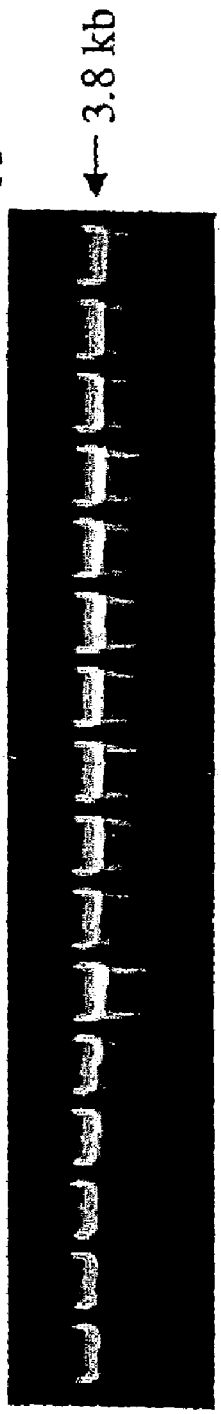
A. pWB407 incubated with no methylene blue
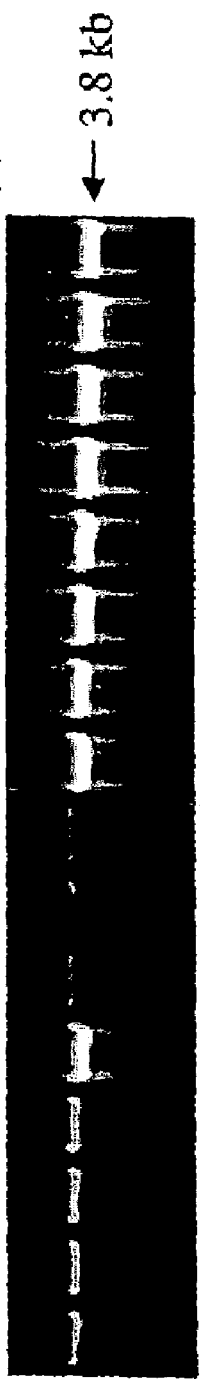
B. pWB407 incubated with 25 μg/mL methylene blue

SEQUENCE LISTING

<160> NUMBER OF SEQ ID NOS: 11

<210> SEQ ID NO 1
<211> LENGTH: 23
<212> TYPE: DNA
<213> ORGANISM: artificial
<220> FEATURE:
<223> OTHER INFORMATION: primer

<400> SEQUENCE: 1
cgaacgtcgc gcagagaaac agg          23

<210> SEQ ID NO 2

```
<211> LENGTH: 20
<212> TYPE: DNA
<213> ORGANISM: artificial
<220> FEATURE:
<223> OTHER INFORMATION: primer

<400> SEQUENCE: 2
cctgctctgc cgcttcacgc                                               20

<210> SEQ ID NO 3
<211> LENGTH: 25
<212> TYPE: DNA
<213> ORGANISM: artificial
<220> FEATURE:
<223> OTHER INFORMATION: primer

<400> SEQUENCE: 3
tttttagcaa tacactacac agcaa                                         25

<210> SEQ ID NO 4
<211> LENGTH: 19
<212> TYPE: DNA
<213> ORGANISM: artificial
<220> FEATURE:
<223> OTHER INFORMATION: primer

<400> SEQUENCE: 4
attacgccaa tcgatcacg                                                19

<210> SEQ ID NO 5
<211> LENGTH: 27
<212> TYPE: DNA
<213> ORGANISM: artificial
<220> FEATURE:
<223> OTHER INFORMATION: primer

<400> SEQUENCE: 5
gcacagaagc tattatgcgt ccccagg                                       27

<210> SEQ ID NO 6
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (6)..(6)
<223> OTHER INFORMATION: 8-oxo-Guanine
<220> FEATURE:
<221> NAME/KEY: misc_feature
<222> LOCATION: (18)..(18)
<223> OTHER INFORMATION: m=c or a

<400> SEQUENCE: 6 gggggggagag tttgatcmtg gctca                                        25

<210> SEQ ID NO 7
<211> LENGTH: 28
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (6)..(6)
<223> OTHER INFORMATION: 8-oxo-Guanine
<220> FEATURE:
<221> NAME/KEY: misc_feature
```

```
<222> LOCATION: (12)..(12)
<223> OTHER INFORMATION: y=c or t

<400> SEQUENCE: 7 gggggggtacg gytaccttgt tacgactt                                          28

<210> SEQ ID NO 8
<211> LENGTH: 24
<212> TYPE: DNA
<213> ORGANISM: artificial
<220> FEATURE:
<223> OTHER INFORMATION: primer

<400> SEQUENCE: 8
ccatgattca gtgtgcccgt ctgg                                               24

<210> SEQ ID NO 9
<211> LENGTH: 29
<212> TYPE: DNA
<213> ORGANISM: artificial
<220> FEATURE:
<223> OTHER INFORMATION: primer

<400> SEQUENCE: 9
tgtcgatcag gatgatctgg acgaagagc                                          29

<210> SEQ ID NO 10
<211> LENGTH: 33
<212> TYPE: DNA
<213> ORGANISM: artificial
<220> FEATURE:
<223> OTHER INFORMATION: primer

<400> SEQUENCE: 10
cgaaagcttt caaggatctt accgctgttg aga                                     33

<210> SEQ ID NO 11
<211> LENGTH: 813
<212> TYPE: DNA
<213> ORGANISM: unknown
<220> FEATURE:
<223> OTHER INFORMATION: Thermus thermophilus endonuclease IV

<400> SEQUENCE: 11
atgccgcgct acgggttcca cctttccatc gccgggaaaa agggcgtggc cggggcggtg        60
gaggaggcca ccgccctcgg cctcaccgct ttccagatct cgccaaaaag cccgcggagc       120
tggcgcccaa gggccctctc cccggccgag gtggaggcct ccgcgccttt aagggaggcc       180
tccgggggcc tccccgccgt gatccacgcc tcctacctgg tcaacctggg ggcggagggg       240
gagctttggg agaagagcgt ggcgagcctg gcggacgacc tggagaaggc cgccctcctc       300
ggggtggagt acgtggtcgt ccaccccggc tcggccgcc cgagcgggt caaggaaggg         360 gccctcaagg ccctgcgcct cgccggcgtc cgctcccgcc ccgtcctcct cgtggagaac       420
accgccgggg gcggggagaa ggtgggggcg cggtttgagg agctcgcctg gctcgtggcg       480 gacaccccc tccaggtctg cctggacacc tgccacgcct acgccgccgg gtacgacgtg       540
gccgaggacc ccttgggggt cctggacgcc ctggaccggg ccgtgggcct ggagcgggtg       600
cccgtggtcc acctcaacga ctccgtgggc ggcctcggaa gccgcgtgga ccaccacgcc       660
cacctcctcc agggaaagat cggggagggg ctcaagcgcg tcttcttgga cccgaggctc       720
```

```
aaggaccggg tcttcatcct ggaaaccccc aggggaccgg aggaggacgc ctggaacctc    780
cgggtcctca gggcctggct cgaggaggcc taa                                 813
```

REPAIR OF NUCLEIC ACIDS FOR IMPROVED AMPLIFICATION

CROSS REFERENCE

This application claims priority from U.S. Provisional Application Ser. No. 60/620,896 filed Oct. 21, 2004, U.S. Provisional Application Ser. No. 60/646,728 filed Jan. 24, 2005 and U.S. Provisional Application Ser. No. 60/673,925 filed Apr. 21, 2005.

BACKGROUND

Various approaches have been reported to repair DNA using base excision enzymes. Unfortunately, these approaches in different ways cause further damage to the DNA. Conventional PCR techniques have been modified to improve amplification in some aspects. U.S. Pat. No. 5,035,996 describes a process for controlling contamination of nucleic acid amplification reactions that uses the modified nucleotide, dUTP, in the amplification reaction. This process uses uracil glycosylase to eliminate those PCR products containing uracil to prevent contaminating subsequent PCR reactions. U.S. patent publication no. 2004-0067559 A1 also relies on modified bases in primer DNA prior to amplification and uses, for example, dUTP for incorporation into the amplicon. The amplicon can then be fragmented by adding, for example, Uracil-DNA Glycosylase (UDG) and Endonucleaese (Endo) IV.

Hot start nucleic acid amplification has been used to lower mis-priming during PCR. One type of hot start amplification relies on the presence of a PCR primer with a blocked 3' terminus to prevent extension by the polymerase present in the PCR reaction (see for example US 2003-0119150). The primer is unblocked by a thermostable 3'-5' exonuclease that is active at >37° C. Therefore, the polymerase will only extend the PCR primers once the exonuclease unblocks the 3' end at >37° C. Alternatively the Taq polymerase is blocked and then activated at amplification temperatures.

Barnes, W. M. *Proc. Natl. Acad. Sci. USA* 91:2216-2220 (1994) describes the use of vent polymerase and Taq polymerase as an improvement over the use of Taq polymerase only in amplification. Ghadessy et al. reported a mutant Taq polymerase that is not halted by damaged or abasic sites (Ghadessy et al. *Nature Biotechnol.* 22(6):755-9 (2004)).

It has been reported that conventional amplification techniques are compromised if the DNA is substantially damaged (DiBernardo et al. *Nucl. Acids Res.* 30:e16 (2002)). Degradation and/or fragmentation of DNA resulting from exposure to the environment and microorganisms which contain DNA endonucleases is a frequent problem in forensics, diagnostic tests and routine amplification and affects fidelity and yield of the amplification product. In addition, the problem of degraded DNA is also faced by researchers who are analyzing the DNA obtained from frozen, extinct or extremely rare organisms.

Fromenty, B., et al. *Nucl. Acids Res.* 28(11):e50 (2000) and International Publication No. WO/0151656 reported that Exonuclease (Exo) III improved yields of long PCR. Fromenty also reported decreased yields of amplicon for DNA<500 bp. One of the problems associated with the use of Exo III is that it degrades template and primers.

Di Benardo et al. *Nucl. Acids Res.* 30(4):e16 (2002) described the use of T4 DNA ligase (T4 ligase) and an *E. coli* polymerase to amplify short regions of single-stranded DNA between cross-linked regions of double-stranded DNA.

Another approach to amplification of damaged DNA has been described in U.S. Publication No. 2003-0077581. Degraded nucleic acid was hybridized to undegraded nucleic acid having a sequence homologous to the degraded nucleic acid. Regions of the degraded nucleic acid were then filled in with nucleotide precursors. The fragmented strands were then covalently linked using a polymerizing and/or ligating enzyme.

Preparations for improving amplification of damaged DNA can be obtained commercially from Sigma, St. Louis, Mo. and Qbiogene, now MP Biomedicals, Irvine, Calif. Although the compositions of these preparations are not provided, it is assumed that Exo III is contained in the preparation. The preparations are not recommended for DNA templates less than 500 base pairs in length.

Others report the use of a combination of *E. coli* DNA Pol I and T4 ligase for pre-amplification repair (Pusch, et al., *Nucl. Acids Res.* 26:857 (1998)). However, according to Pusch et al. the preamplification product is purified before initiation of amplification.

SUMMARY

In an embodiment of the invention, a method is provided for enhancing at least one of fidelity and yield of an amplification product of a damaged polynucleotide, that includes the steps of: (a) incubating the polynucleotide in a reaction mixture comprising a ligase and a cofactor selected from NAD+ or ATP and excluding Endo VI; (b) permitting amplification of the polynucleotide to occur in the reaction mixture by the addition of amplification reagents to the reaction mixture during or after step (a); and (c) enhancing at least one of fidelity or yield of the amplification product in the presence of step (a) compared to in the absence of step (a).

The above method is not particularly time sensitive in respect to whether the incubation occurs in seconds, minutes or hours. The ligase used in embodiments of the method may be mesophilic or thermophilic and does not exclude cryophilic ligases, which might be useful under particular circumstances. The choice of ligase with respect to temperature sensitivity depends on what is best suited for a particular set of reaction conditions. For example, if the amplification reagents are added during the incubation step (a), then it may be desirable to employ a thermophilic ligase to withstand temperatures utilized during amplification. Examples of thermophilic ligases are Taq DNA ligase (Taq ligase) and 9° N ligase. Taq ligase is more effective with a NAD$^+$ cofactor while 9° N DNA ligase (9° N ligase) is more effective with an ATP cofactor. Examples of a mesophilic ligase are T4 ligase (using an ATP cofactor) and *E. coli* DNA ligase (*E. coli* ligase)(using an NAD$^+$ cofactor).

The reaction mixture may further include an AP endonuclease such as Type II endonuclease, T7 Endonuclease (Endo) I or mutant thereof or Endo IV. The reaction mixture may alternatively or also include a polymerase for example Taq polymerase, an *E. coli* polymerase, a *Thermomicrobium* sp. polymerase or an archaeal polymerase or mutant thereof such as Pfu, Vent®, Deep Vent®, 9° N or GBD polymerase.

In embodiments of the invention, enzymes that may be additionally added to the reagent mixture include T4 pyrimidine dimer glycosylase, [fapy]-DNA glycosylase (Fpg), at least one of UvrA, UvrB, UvrC, UvrD, Cho, UDG, Aag, Endo III and Endo V in various combinations depending on the type of damage sustained by the polynucleotide.

In an embodiment of the invention, a reaction mixture is used containing about 1-100 units of endonuclease, about 0.05-0.25 units of polymerase and about 5-500 units of ligase optionally added to 1-1000 ng DNA.

Types of damage that may affect a polynucleotide include apurinic/apyrimidinic (AP) sites, mutagenized nucleotides, modified nucleotides, nicks, gaps and DNA-DNA or DNA-protein cross-links.

The damaged polynucleotide may be obtained from natural sources, preserved biological material, forensic evidence, ancient polynucleotides, a tissue biopsy or routine biological manipulation.

According to embodiments of the method, amplification of DNA is achieved by any of PCR amplification, helicase-dependent amplification, transcription-mediated amplification, strand-displacement amplification, rolling circle amplification and whole genome amplification.

Where the polynucleotide is a single-stranded RNA, the amplification may be a reverse transcriptase dependent amplification.

In an embodiment of the method, the polynucleotide is capable of producing an amplicon in a size range of 50 nucleotides to 100,000 nucleotides for PCR amplification.

In an embodiment of the invention, an amplification kit is provided that includes instructions for use and one or more enzymes wherein at least one of the enzymes is a ligase, the one or more enzyme being formulated for addition to an amplification mixture to enhance amplification or for use prior to addition of the amplification mixture to enhance amplification.

In another embodiment of the invention, a composition is provided that contains an effective amount of a ligase, a polymerase, and an AP endonuclease not including Endo VI, the mixture being capable of enhancing at least one of yield and fidelity of amplification of a polynucleotide compared with amplification of the polynucleotide in the absence of the composition. For example, concentrations of reagents in the composition include: an AP endonuclease at a concentration of 1-100 units of endonuclease, a polymerase at 0.05-0.25 units, and 5-500 units of ligase contained for example in a reaction volume of 10-100 μl. This formulation may be applied to 1-1000 ng DNA for repairing the DNA. For larger concentrations of DNA, the amounts of enzymes should be increased proportionally. In embodiments of the invention, additional enzymes may be included in the composition including one or more of T4 pyrimidine dimer glycosylase, [fapy]-DNA glycosylase (Fpg), UvrA, UvrB, UvrC, UvrD, Cho, UDG, Aag, Endo III and Endo V in various combinations depending on the type of damage sustained by the polynucleotide.

LIST OF FIGURES

FIGS. 1A-1D show enhanced amplicon yield from heat-damaged lambda DNA after preincubation with specified enzymes.

FIG. 1A shows DNA template damaged by heat to differing extents and the effect of this damage on amplification of a 5 kb segment of lambda DNA where 5 ng, 2 ng and 1 ng of heat-treated lambda DNA was amplified after prior damage by 99° C. heat treatment for 0 sec, 30 sec, 60 sec, 90 sec, 120 sec or 180 sec. The damaged DNA was not subjected to enzyme treatment prior to amplification. The amount of amplification was determined after electrophoresis and was found to be substantially reduced by 120 sec heat treatment. The first and last lanes on the gel contain 1 μg of a 2-log ladder size standard (NEB#N3200, New England Biolabs, Inc., Ipswich, Mass.).

FIG. 1B shows increased amplicon yields from heat-damaged lambda DNA using Taq ligase, *E. coli* Endo IV and *E. coli* PolI on amplification of a 5 kb segment of lambda DNA. DNA was heat damaged as described in FIG. 1A but the damaged DNA was subjected to enzyme treatment prior to amplification. The results of amplification are shown after a 10-minute pretreatment reaction with Taq ligase, *E. coli* Endo IV and *E. coli* PolI. The amplicon yield was increased throughout but was especially noticeable with 120 sec and 180 sec heat damaged DNA.

FIG. 1C shows increased amplicon yields from heat-damaged lambda DNA using Taq ligase, Tth Endo IV and *E. coli* PolI. The amplification was performed according to FIG. 1B but the enzyme treatment prior to amplification contained *Thermus thermophilus* (Tth) Endo IV in place of *E. coli* Endo IV. The results of amplification are shown after a 10-minute pretreatment reaction with *Thermus aquaticus* (Taq) ligase, Tth Endo IV and *E. coli* PolI. The amplicon yield was increased throughout but was especially noticeable with 120 sec and 180 sec heat-damaged DNA. Only the first lane contains the size ladder.

FIG. 1D shows increased amplicon yields from heat-damaged lambda DNA using *E. coli* ligase, *E. coli* Endo IV and *E. coli* DNA polI. The amplification was performed according to FIG. 1B but the enzyme treatment prior to amplification contained *E. coli* ligase in place of Taq ligase. The lambda DNA subjected to 99° C. for 180 sec was used as a template. The amount of template DNA used is indicated above each lane. The yield of amplicon is increased for each of the template amounts by enzyme pretreatment.

FIGS. 2A-2B shows the effect of citrate treatment of template DNA on amplicon yield.

FIG. 2A shows the results of amplification of a 5 kb segment of lambda DNA where lambda DNA was heated to 70° C. in citrate buffer for 0, 20, 40, 80, 120, and 160 minutes. 50 ng, 10 ng and 5 ng of each heat-treated sample were amplified and the resulting products were visualized on a gel to determine the extent of amplification. The DNA was not treated with selected enzymes prior to amplification. The last lane on the right contains 1 μg of 2-log ladder.

FIG. 2B shows the increase in yield of a 5 kb amplicon of lambda DNA regardless of which polymerase was used in the enzyme mixture. 120-minute heat/citrate-damaged lambda DNA as treated with various enzymes prior to amplification.

Lane 1: 1 μg 2-log ladder (NEB# N3200, New England Biolabs, Inc., Ipswich, Mass.).

Lane 2: no pretreatment.

Lane 3: Pretreatment with Taq ligase, Taq DNA polymerase and *E. coli* Endo IV.

Lane 4: Pretreatment with Taq ligase, *E. coli* PolI, and *E. coli* Endo IV.

Lane 5: Pretreatment with Taq ligase, Taq:Vent® DNA polymerase mix, and *E. coli* Endo IV.

FIG. 3 shows the results of amplification of a 200 bp segment of krill genome that has been extracted from an ethanol stored sample of krill and pretreated with an enzyme mixture containing one of various polymerases, a ligase and an AP endonuclease that enhances amplification yields.

Lane 1: No pretreatment of krill DNA with enzymes.

Lane 2: Pretreatment of krill DNA with Taq ligase, *E. coli* Endo IV, and Taq polymerase.

Lane 3: Pretreatment of krill DNA with Taq ligase, *E. coli* Endo IV, and Vent® polymerase.

Lane 4: Pretreatment of krill DNA with Taq ligase, *E. coli* Endo IV, and 50:1 Taq:Vent® polymerase.

FIG. 4 shows an increase in yield of a 10 kb amplicon from heat-damaged DNA. 180 sec heat-damaged DNA was pretreated with an enzyme mixture and then amplified.

Lane 1: 1 μg of a 2-log ladder size standard (NEB#N3200, New England Biolabs, Inc., Ipswich, Mass.).

Lane 2: Pre-treatment with Taq ligase, *E. coli* Endo IV, and *E. coli* PolI.

Lane 3: Pre-treatment with Taq ligase and *E. coli* Endo IV.

Lane 4: Pretreatment with Taq ligase.

Lane 5: Control-untreated DNA.

FIG. 5 shows that ligase pretreatment increases amplicon yield from environmental DNA (soil sample extract).

Lane 1: A 2-log ladder size standard (NEB# N3200, New England Biolabs, Inc., Ipswich, Mass.).

Lane 1: No enzyme pretreatment.

Lane 2: Pre-treatment with T4 ligase.

Lane 3: No enzyme pre-treatment.

Lane 4: Pretreatment with Taq ligase.

FIG. 6: Genbank search revealing proteins with sequence homology with T4 ligase.

FIG. 7: DNA sequence of Tth Endo IV (SEQ ID NO:11).

FIG. 8 shows the effect of UV light on amplicon yield using lambda DNA as a template by gel electrophoresis.

A: Lambda DNA is subjected to UV irradiation for up to 50 sec and a slight reduction in yield of a 2 Kb amplicon produced is shown.

B: Lambda DNA is subjected to UV irradiation for up to 50 seconds and the reduction in yield of a 5 kb amplicon is shown.

C: The effect of various reaction mixtures added to lambda DNA on yield of a 5 kb amplicon after UV irradiation is shown.

Lanes 2-7 are controls in the absence of a reaction mixture.

Lanes 8-13 show the increased beneficial effect of adding ligase, polymerase and AP endonuclease plus 10 Units of T4 PDG.

Lanes 14-19 show the increased beneficial effect of adding ligase, polymerase and AP endonuclease plus 80 units of T4 PDG.

Lanes 1 and 20: A 2-log ladder size standard (NEB#N3200, New England Biolabs, Inc., Ipswich, Mass.).

FIGS. 9A-9B shows that adding ligase to T7 Endo I expands the useful range of the enzyme:DNA ratio to facilitate the removal of heteroduplexes from the amplification mixture so as to increase the ratio of correct sequences. Taq ligase and T7 Endo I were added to supercoiled DNA in varying amounts as indicated for each lane.

FIG. 9a is the control in which no Taq ligase has been added but increasing amounts of T7 Endo I are used. The supercoiled DNA is predominantly cleaved into fragments of various sizes with 12.5-25 units of T7 Endo I.

FIG. 9b shows how the addition of 100 units of Taq ligase protects DNA from non-specific cleavage in the presence of T7 Endo I such that even at 200 units of T7 Endo I, there is a clear band corresponding to linear DNA not present in the absence of ligase.

FIG. 10 shows the effect of repair enzyme treatment on amplicon yield from oxidatively damaged DNA or undamaged template.

FIG. 10A shows that the addition of repair enzymes to an undamaged template, pWB407 has no effect on amplicon yield.

FIG. 10B shows that the addition of Fpg to a damaged template, plasmid pWB407, incubated in the presence of methylene blue, gives inconsistent effects on yield. The addition of Taq ligase, *E. coli* DNA polymerase, and *E. coli* Endo IV in the presence or absence of Fpg increases amplicon yield consistently.

Figure 11:

FIG. 11 shows increased PCR reaction accuracy from damaged DNA after treatment with repair enzymes. Repair enzyme treatment of undamaged template, plasmid pWB407, prior to PCR has no significant effect on reaction accuracy. Treatment of a damaged template, plasmid pWB407 incubated with methylene blue, with Fpg alone or also with Taq ligase, *E. coli* DNA polymerase I, and *E. coli* endonuclease increases the accuracy of PCR. The measure of accuracy is the number of white colonies verses the number of blue colonies after cloning a lacZ-containing amplicon as discussed below. The higher the percentage of white colonies the greater the error rate.

Figure 12:
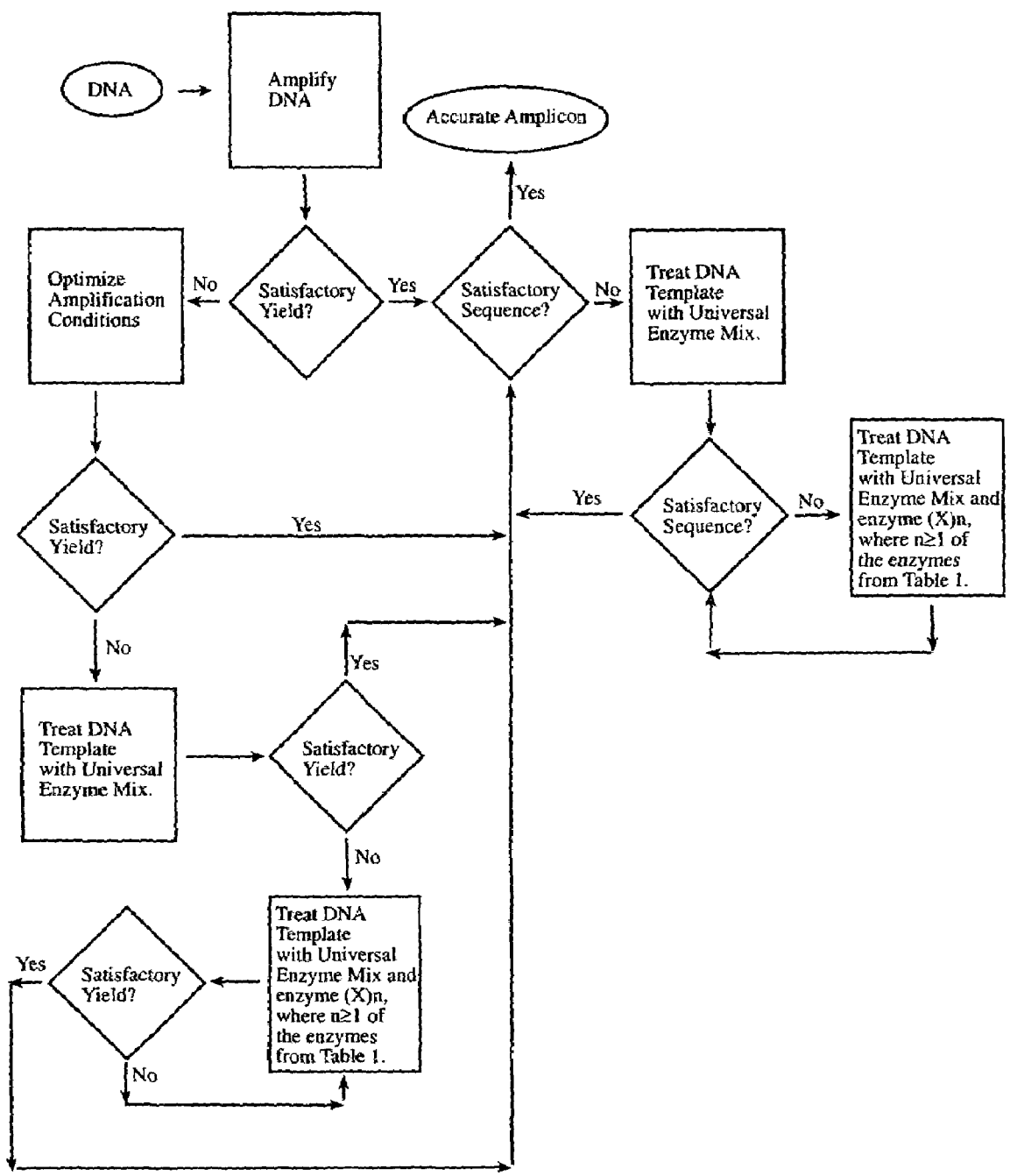

FIG. 12 shows a flow diagram for treating DNA with unknown damage to increase at least of one of fidelity and yield.

DESCRIPTION

Embodiments of the invention describe methods for improving at least one of yield or fidelity for synthesis of damaged polynucleotides. Where polynucleotide synthesis leads to polymerase-dependent amplification, short amplicons that are less than about 500 bases in length (as short as 100 nt) or long amplicons that are greater than 500 bases or as much as about 100 kb may be amplified (for PCR amplification). Other types of polynucleotide synthesis include primer extension reactions such as amplification (for example PCR, RT-PCR, and QPCR), genome amplification, rolling circle amplification (RCA) and helicase-dependent amplification (HDA); and DNA sequencing reactions. Embodiments of the methods have wide utility in molecular biology research and in solving problems in applied biology, for example, in forensics, in biological archeology in which it is desirable to analyze DNA from ancient sources, for taxonomy where it is desirable to analyze DNA from environmental samples such as required for the Barcode of Life Project, for diagnostic assays including tissue biopsies to determine a disease susceptibility or status and for molecular biology research.

Source and Extent of Damage

Damage sustained by polynucleotide molecules is common even in "normal" polynucleotides although damage is more severe in preserved tissues, dried specimens or polynucleotides that are exposed to the environment. Damage can occur as a result of the age of the sample or its length, its source or its preparation. In addition, damage can occur during the application of a methodology for polynucleotide synthesis such as occurs during PCR amplification, which involves a high temperature step.

Polynucleotides can sustain damage in a variety of ways. Various types of damage include: (a) apurinic or apyrimidinic damage caused for example by heat, storage of polynucleotides in ethanol, and exposure to factors in the environment such as $H_2O$, pH etc; (b) modification of individual nucleotides, caused for example by deamination, alkylation, oxidation and dimerization; (c) nicks and gaps caused for example by heat, storage of polynucleotide in ethanol, and exposure to factors in the environment such as $H_2O$, pH etc; (d) cross-linking caused for example, by formaldehyde, environmental factors, and ethanol storage; and (e) mismatched DNA caused by for example misincorporation of a nucleotide by a polymerase.

Different polynucleotide preparations will experience different types of damage resulting from, for example, storage or handling of the polynucleotide preparation in vitro, and may depend on how prokaryotic cells, archaea or eukaryotic cells containing the polynucleotides are stored and the characteristics of the cells from which the polynucleotide is extracted.

Definitions

The term "polynucleotide" refers to double-stranded DNA, double-stranded RNA, hybrid DNA/RNA duplex, single-stranded DNA and single-stranded RNA.

A "repair enzyme" refers to a cryophilic, mesophilic or thermophilic enzyme that participates in the process of repair of a polynucleotide. For example, a repair enzyme may induce breakage of the polynucleotide at a bond, thereby facilitating removal of damaged regions of the polynucleotide. Enzymes with a synthetic role such as ligases and polymerases are also repair enzymes.

DNA repair enzymes are described in the scientific literature, for example, see Wood, R. D., et al. *Mutat. Res.* 577(1-2):275-83 (2005) and Eisen, J. A. and Hanawalt, P. C. *Mutat. Res.* 435(3):171-213 (1999). A list of human repair enzymes is provided in Table 1. Although not described in Table 1, the homologs of the listed enzymes and other functionally related enzymes are included in the definition of repair enzymes. Any of the above enzymes may be naturally occurring, recombinant or synthetic. Any of the enzymes may be a native or in vitro-created chimera with several activities. In addition to the enzymes described above, it is known to a person of ordinary skill in the art how to search the databases to identify other related enzymes that share conserved sequence motifs and have similar enzyme activity. For example, the NCBI web site (www.ncbi.com) provides a conserved domain database. If, for example, the database is searched for homologs of Endo IV, 74 sequence matches are recovered. (Also see FIG. 6 for ligases).

A "polynucleotide cleavage enzyme" used in enzyme mixtures for repairing damaged DNA is a class of repair enzymes and includes AP endonucleases, glycosylases and lyases responsible for base excision repair.

A damaged base can be removed by a DNA glycosylase enzyme which hydrolyses an N-glycosylic bond between the deoxyribose sugar moiety and the base. The product of this reaction is an apurinic or apyrimidinic site (AP site) that must be correctly filled. This can be achieved by an endonuclease, which nicks the sugar phosphate backbone adjacent to the AP site. The abasic sugar is removed and a new nucleotide is inserted by polymerase/ligase activity. Some enzymes having applicability herein have glycosylase and AP endonuclease activity in one molecule. These repair enzymes are found in prokaryotic and eucaryotic cells. Abasic sites can be recognized and cleaved by AP endonucleases and/or AP lyases. Class II AP endonucleases cleave at AP sites to leave a 3' OH that can be used in polynucleotide polymerization. Furthermore, AP endonucleases can remove moieties attached to the 3' OH that inhibit polynucleotide polymerization. For example a 3' phosphate can be converted to a 3' OH by *E. coli* Endo IV. AP endonucleases can work in conjunction with glycosylases.

Examples of glycosylase specificities include Uracil, Hypoxanthine, 3-methyladenine (3-mAde), Formamidopyrimidine and Hydroxymethyluracil. The presence of Uracil in DNA occurs due to mis-incorporation or deamination of cytosine by bisulfate, nitrous acids, or spontaneous deamination. Hypoxanthine occurs due to deamination of adenine by nitrous acids or spontaneous deamination. 3-mAde is a product of alkylating agents. *E. coli* has two 3-mAde glycosylase called TagI and TagII. Formamidopyrimidine (FAPY)(7-mGua) is the most common product of methylating agents of DNA. Gamma radiation produces 4.6-diamino-5-FAPY. An *E. coli* glycosylase that repairs this lesion is Fpg endonuclease. Hydroxymethyuricil is created by ionizing radiation or oxidative damage to thymidine.

Lyases break the phosphodiester bond in a polynucleotide. Examples of AP endonucleases belong to 4 classes.

(I) cleaves 3'→3'-OH+5'-P— and has associated glycosylase activity.

(II) cleaves 5'→3'-OH+5'-P (III) cleaves 3'→3'-P+5'-OH (IV) cleaves 5'→3'-P+5'-OH Several enzymes have been isolated that appear to have AP endonuclease or lyase and glycosylase activities that are coordinated in a concerted manner (i.e., without causing AP site formation) or sequentially.

Examples of polynucleotide cleavage enzymes for use in enhancing at least one of yield and fidelity in an amplification reaction include: 1) AP endonucleases, such as *E. coli* Endo IV, Tth Endo IV, and human AP endonuclease; 2) glycosylases, such as UDG, *E. coli* AlkA and human Aag; and 3) glycosylase/lyases, such as *E. coli* Endo III, *E. coli* Endo V, *E. coli* Endo VIII, *E. coli* Fpg, human OGG1, T4 pyrimidine dimer glycosylase (T4 pdg) and human AP endonuclease.

Endo VI (also termed Exo VI) is capable of degrading a substantial portion of a polynucleotide outside the damaged regions in a polynucleotide under normal reaction conditions in a few hours and is not included in enzyme mixtures for treating damaged polynucleotides.

A "polymerase" as used in enzyme mixtures herein refers to an enzyme that contains polymerase activity. The repair and amplifying polymerases can be the same or different.

Examples of polymerases include thermostable bacterial polymerases such as Taq polymerase and archeal polymerases such as Vent®, deep Vent® and Pfu; and thermolabile enzymes such as Bst polymerase, *E. coli* PolI, *thermomicrobium roseum* polymerase and *thermomicrobium thermophilus*, phage polymerases such as phi29 polymerase, T7 polymerase and T4 polymerase etc., or mutants, derivatives or modifications therefrom. Examples of derivatives include Pfusion™ enzyme (Finnzymes, Espoo, Finland) and other polymerases that combine a double strand binding protein with polymerase sequences from one or several sources.

A "ligase" as used in the enzyme mixtures described here refers to an enzyme that joins a 5' end of a single strand of a polynucleotide to a 3' end of another single strand of a polynucleotide. Such ligases are found in substantially all eukaryotic cells as well as prokaryotic cells, viruses and archaea. Any of these ligases can be used in repair as described herein. Examples of ligases include 9° N ligase, *E. coli* ligase, T4 ligase and Taq ligase. Other ligases include LIGA (NP-416906.1), TthDNALGS (AAA27486.1), LIG3 (NM-013975) and LIG4 (NM-002312).

Other ligases or ligase-like proteins that may have utility herein are revealed by a Genbank search using T4 ligase or *E. coli* ligase to search the database (see FIG. 6) in which any enzyme sharing at least 6 contiguous amino acids with these known ligases may be included in a repair mixture according to embodiments of the invention.

Contrary to a published use of ligase in combination with Exo III in the absence of any cofactors (U.S. Publication No. 2005-0026147), it has been found here that NAD+ or ATP is required in enzyme mixtures that include ligase. More specifically, Taq ligase and *E. coli* ligase require NAD+while T4 ligase and 9° N ligase require ATP.

Exemplified ligases, polymerases and endonucleases are available from New England Biolabs Inc. where pages 107-117 of the 2005-2006 catalog are incorporated by reference (pp. 102-108 for ligases), U.S. Provisional Application No. 60/717,296 and International Publication No. WO 2005/052124. In addition, thermostable repair enzymes can be used interchangeably with thermolabile repair enzymes in a preamplification mixture. Thermostable enzymes are active at above 40° C. or more particularly 65° C. or above.

Embodiments of present methods improve the yield or fidelity of products resulting from polynucleotide amplification or other synthesis reaction. This can be achieved, for example, when a damaged polynucleotide is treated with a preparation of enzyme(s) in a pre-incubation mixture and/or during amplification.

Amplification protocols that may benefit from the above described pre-incubation include polymerase chain reaction (PCR), Strand-Displacement Amplifcation (SDA)(U.S. Pat. Nos. 5,455,166 and 5,470,723); HDA (U.S. Publication No. 2004-0058378-A1); Transcription-Mediated Amplification (TMA)(Guatelli et al., *Proc. Natl. Acad. Sci. USA* 87:1874-1878 (1990)); Rolling Circle Amplification (RCA) which generates multiple copies of a sequence for the use in in vitro DNA amplification adapted from in vivo rolling circle DNA replication (see, for example, Fire and Xu, *Proc. Natl. Acad. Sci. USA* 92:4641-4645 (1995); Lui, et al., *J. Am. Chem. Soc.* 118:1587-1594 (1996); Lizardi, et al., *Nature Genetics* 19:225-232 (1998)) and whole genome amplification methods.

A universal enzyme mixture has been found to be useful in a reaction mixture for repairing damaged polynucleotides prior to or during amplification regardless of the type of damage to the polynucleotide. The mixture repairs damaged DNA without causing further damage.

The universal enzyme mixture contains a ligase and a cofactor such as NAD+ or ATP. The mixture preferably additionally includes a polymerase and an AP endonuclease as defined above within a suitable buffer such as Thermopol (New England Biolabs, Inc., Ipswich, Mass.), AccuTaq LA DNA polymerase buffer (Takara Bio Inc., Shiga, Japan) or any other standard Taq buffer. In various embodiments, the universal enzyme mixture contains *E. coli* PolI or Taq polymerase and an AP endonuclease such as a mesophilic Endo IV, e.g., *E. coli* Endo IV or a thermophilic Endo IV, e.g., Tth Endo IV and a ligase selected from *E. coli* ligase, Taq ligase or an archaeal ligase such as 9° N ligase. In a particular embodiment, the enzyme mixture contains 1-100 units Endo IV, 0.05-0.25 units *E. coli* PolI, and 5-500 units of a ligase suitable for repairing 1-1000 ng DNA prior to or during amplification. It will be understood that the concentration range for endonucleases and polymerases other than those specified in the universal mixture above may vary with the enzyme used and the temperature of the reaction. However, the concentration range can be readily ascertained using the assays described in the Examples. For example, a standard preparation of lambda DNA can be heat treated according to Example 1. The DNA can then be subjected to a series of enzyme mixtures containing ligase and cofactors. An additional enzyme is titrated to determine a preferred concentration for that enzyme in the mixture. In this way, DNA repair can be optimized. After amplification of each sample, the amount of the amplified DNA can be determined by gel electrophoresis revealing the preferred concentration range for the test enzyme.

The universal enzyme mixture can be used prior to or during polynucleotide amplification or other synthesis.

As demonstrated in the Examples, depending on the type of damage, it may be desirable to supplement the universal enzyme mixture with additional repair enzymes depending on the nature of the DNA damage. The utility of individual repair enzymes or mixtures of repair enzymes can be determined using the assays described in the Examples and in the Figures to determine their suitability for repairing a particular polynucleotide.

Repair of General or Specific Damage to Polynucleotides (a) General Damage

Determining the nature of damage in a polynucleotide is time-consuming. If some form of damage to a polynucleotide is suspected, for example, the polynucleotide is poorly amplified, it is preferable not to have to identify the lesion or lesions. In these circumstances, a universal mix of enzymes such as described above may be utilized to determine whether improved amplification is obtained. If the improvement is sufficient using the universal mixture then no further action is required. If the improvement is not sufficient, additional enzymes can be added to the mixture as described herein until the preferred result is obtained. The entire assay may be achieved in a single reaction vessel such as a 96 well dish. Each micro-well in the dish is available for a different enzyme mixture including the universal mixture plus enzymes selected to address each class of damage outlined below.

The protocol for selecting enzymes for repair of general damage or unknown damage of DNA is provided in FIG. 12 (flow chart) and in the assays described in the Examples.

(b) Specific Damage

In some circumstances, the nature of the damage to a polynucleotide might be known. In these circumstances, a mixture of enzymes can be selected without undertaking the analysis of FIG. 12.

(i) AP Sites

The loss of a base is the most common spontaneous form of DNA damage. Polymerases and polymerase-based techniques are adversely affected by the presence of these abasic sites. The effectiveness of primer extension reactions is enhanced by repairing any abasic sites found in a polynucleotide. This is achieved in one embodiment by Endo IV activity that cleaves the phosphate backbone at the abasic site. This leaves an extendable 3' OH on the DNA fragment 5' to the cleaved abasic site. It also leaves a deoxyribose-5'-phosphate (dR5P) on the DNA fragment 3' to the cleaved abasic site. A polymerase can extend from the free 3' OH replacing the cleaved abasic site with a correct nucleotide. The dR5P may be removed by an enzyme that specifically targets dR5Ps by a flap endonuclease activity present in certain polymerases such as *E. coli* DNA polymerase I or a separate flap endonuclease such as FENI. The removal of dR5P can also occur by cleavage downstream of this group by the flap endonuclease activity. After removal of the dR5P and the generation of a 5' phosphate adjacent to the 3' OH, a ligase can seal this nick finishing the repair (see Examples 1-3 and 7).

(ii) Modified Nucleotides (a) Thymidine Dimers

Light can damage DNA by inducing the formation of pyrimidine dimers. Pyrimidine dimers block the DNA extension reaction catalyzed by DNA polymerases such as Taq DNA polymerase and hence inhibit DNA amplification (Wellinger, et al. *Nucleic Acids Res.* 24(8):1578-79 (1996)). Consequently it is desirable to repair pyrimidine primers prior to or during amplification. This can be achieved by adding a pyrimidine dimer glycosylase/lyase (Vande Berg, et al. *J. Biol. Chem.* 273(32):20276-20284 (1998)) to the universal enzyme mixture. The DNA backbone is cleaved 5' to the pyrimidine dimer and leaves a 3' hydroxyl moiety that is extendable by a DNA polymerase. In certain embodiments, extension at the 3' hydroxyl and subsequent formation and then cleavage of the lesion-containing flap generated during DNA extension results in a nick that is sealed by an enzyme capable of sealing the nick. Cleavage of the flap can be achieved by the extending polymerase for example, E. coli polymerase I or by the action of a flap endonuclease ((Xu, Y., et al. *J. Biol. Chem.* 275(27):20949-20955 (2000), Liu, Y., et al., *Annu. Rev. Biochem.* 73:589-615 (2004)).

(b) Oxidative Damage

Inaccuracies can be introduced into the products of DNA amplification reactions because of undesired nucleotide incorporation opposite a damaged base (Gilbert, et al. *Am. J. Hum. Gen.* 72:48-61 (2003); Hofreiter et al. *Nucl. Acids Res.* 29:4793-9 (2001)). These inaccuracies can be discovered by amplifying, cloning and sequencing the same sample many times. Inaccuracies due to base damage can also be identified by comparing sequence data before and after sample treatment with an enzyme such as UDG, which removes one of the common types of mutagenic DNA lesions (Hofreiter, et al. *Nucl. Acids Res* 29:4793-9 (2001)). However, treatment with UDG creates an abasic site within the DNA that inhibits DNA amplification by primer extension. This creates problems for rare DNA samples that may be made refractory to amplification by UDG treatment.

Modified nucleotides that are the product of oxidative damage can be removed from the polynucleotide by Fpg or hOGG to leave a blocked polynucleotide where the blocked polynucleotide is repairable by an AP endonuclease such as Endo IV.

The effectiveness of enzyme pretreatment to repair oxidative damage to a polynucleotide prior to amplification is illustrated in Example 9 where the universal enzyme mixture is supplemented with Fpg in the pre-incubation mixture.

Other modified nucleotides such as alkylated bases or deaminated bases where cytosine is converted to uracil, guanine to xanthine or adenine to hypoxanthine give rise to miscoding.

Removal of these modified nucleotides is desirable. These modified bases can be removed by any of AlkA, UDG or Aag as described in Example 10, leaving an AP site. This AP site can then be repaired by a reaction mixture containing a ligase and preferably also an AP endonuclease and a polymerase. Removal of a uracil enables a polymerase in an amplification reaction that would normally be stopped at this site to continue amplifying the DNA. For example, Vent® polymerase activity is inhibited by an incorrect uracil inserted into the DNA. The ability to remove the uracil permits the polymerase to have enhanced effectiveness.

(iii) Nicks and Gaps

Nicks and gaps in the DNA backbone can lead to truncated primer extension products and inhibit amplification reactions. The concerted action of a ligase and a polymerase in the universal enzyme mixture repairs nicks and gaps in the DNA thus enhancing DNA amplification reactions.

(iv) Cross-Links

Additional nucleotide excision repair (NER) proteins (Minko et al. *Biochemistry* 44:3000-3009 (2005); Costa et al. *Biochimie* 85(11):1083-1099 (2003); Sancar *Ann. Rev. Biochem* 65:43-81 (1996)) can be added to the Universal enzyme mixture to repair damage resulting from exposure of polynucleotides to formaldehyde and bulky adducts as well as damage that results in chemically-modified bases that form DNA-protein cross-links. At least one of *E. coli* UvrA, UvrB, mutant UvrB, UvrC, UvrD or Cho (Moolenar et al. *Proc. Natl Acad. Sci USA* 99:1467-72 (2002)) can be used to make incisions at the 5' end and optionally the 3' end around a damaged site. Details about the properties and purification protocols of these enzymes can be obtained from (Zou, Y., et al. *Biochemistry* 43:4196-4205 (2004)). The repair process can be completed by means of a DNA polymerase, a DNA ligase and optionally a flap endonuclease.

The generation of a 3' hydroxyl at a 5' incision site can be useful if the NER enzyme(s) cleave the DNA but leave a blocked 3' end on the DNA that inhibits primer extension. An example would be if the NER enzyme(s) cleaved the DNA and left a 3' phosphate. This would not be extendable by known DNA polymerases unless the 3' phosphate was removed by for example, *E. coli* Endo IV.

If the NER enzyme or enzymes cleaves 5' and 3' to the DNA lesion then the damage is removed when the newly released oligonucleotide dissociates from the DNA. A polymerase can simply fill in the excised region of DNA leaving a nick which ligase then seals to complete the repair. In certain cases the polymerase may fill in the DNA and then proceeds to displace the remaining DNA strand. In these circumstances, an enzyme with flapase activity permits a nick to be formed that a ligase can seal. In cases in which the NER enzyme or enzymes only cleaves 5' to the damage, the polymerase preferably displaces the original DNA strand until it is past the damage at which point a flapase cleaves the DNA flap to create a ligatable nick. The flapase may be active before and after the DNA lesion is reached. Preferably, the polymerase and flapase activities work to eventually displace and remove the DNA lesion leaving a ligatable nick, thus repairing the DNA template. An example of the effectiveness of the above approach is provided in Example 7.

(v) Mismatched Polynucleotides

Heteroduplex DNA can be a problem in multi-template PCR and in homogeneous template PCR (Lowell, J. L. & Klein, D. A. *Biotechniques* 28:676-681 (2000); Thompson, J. R., et al. *Nucl. Acids Res.* 30(9):2083-2088 (2002); Smith, J. & Modrich, P. *Proc. Natl. Acad. Sci. USA* 94:6847-6850 (1997)). T7 Endo I or mutant thereof can be used together with a ligase to remove mismatch regions. This approach does not require quantitation of DNA and avoids the extra steps after the PCR reaction required by Lowell, et al. *Biotechniques* 28:676-681 (2000); and Smith, et al. *Proc. Natl. Acad. Sci. USA* 94:6847-6850 (1997). An example of the use of these enzymes is provided in Example 8. The useful range of the T7 endonuclease or mutant:DNA ratio can be expanded by including a DNA ligase activity to minimize non-specific cleavage in the heteroduplex cleavage reaction.

Discussion of the Examples and Figures

Figure 1A:
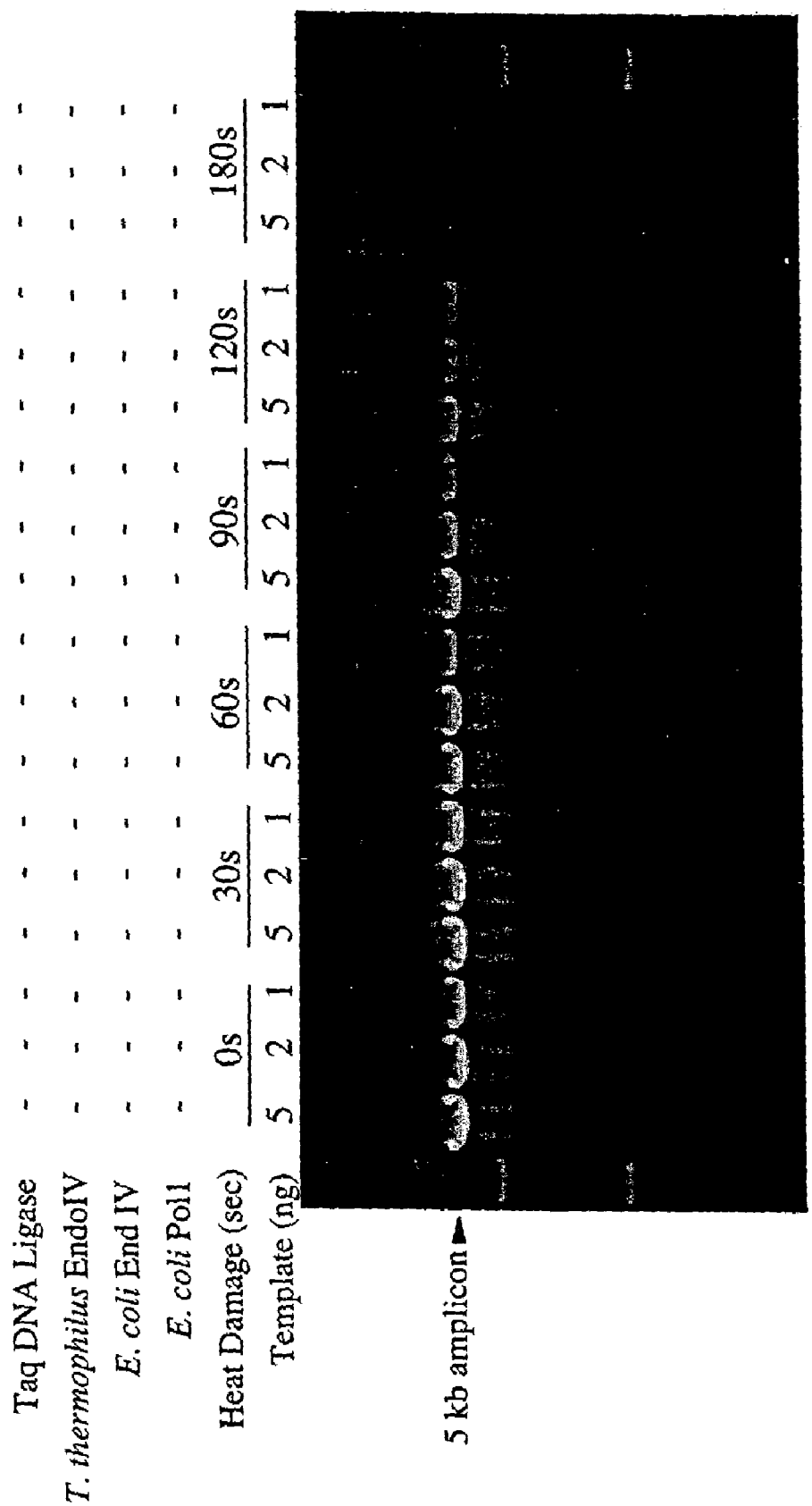

Example 1 and FIGS. 1A-1D show that amplicon yields obtained from PCR amplification are substantially negatively affected when the template DNA is damaged beyond a certain threshold of damage (e.g., about 90 seconds heat treatment) (see FIG. 1A). The effect of this damage on amplification can be reversed and amplicon yields enhanced by incubating the DNA with a mixture of enzymes before amplification (see FIGS. 1B, 1C and 1D). In addition, amplicon yields of "undamaged" DNA can be enhanced by adding the enzyme mixture described.

Example 1 shows that the effect of the enzyme mixture on amplification of DNA is not dependent on a single type of AP endonuclease or ligase, but instead endonucleases or ligases from multiple alternative sources can be used. For example, thermostable Tth Endo IV was found to be as effective as *E. coli* Endo IV and *E. coli* ligase was as effective as the thermostable Taq ligase.

Figure 2B:
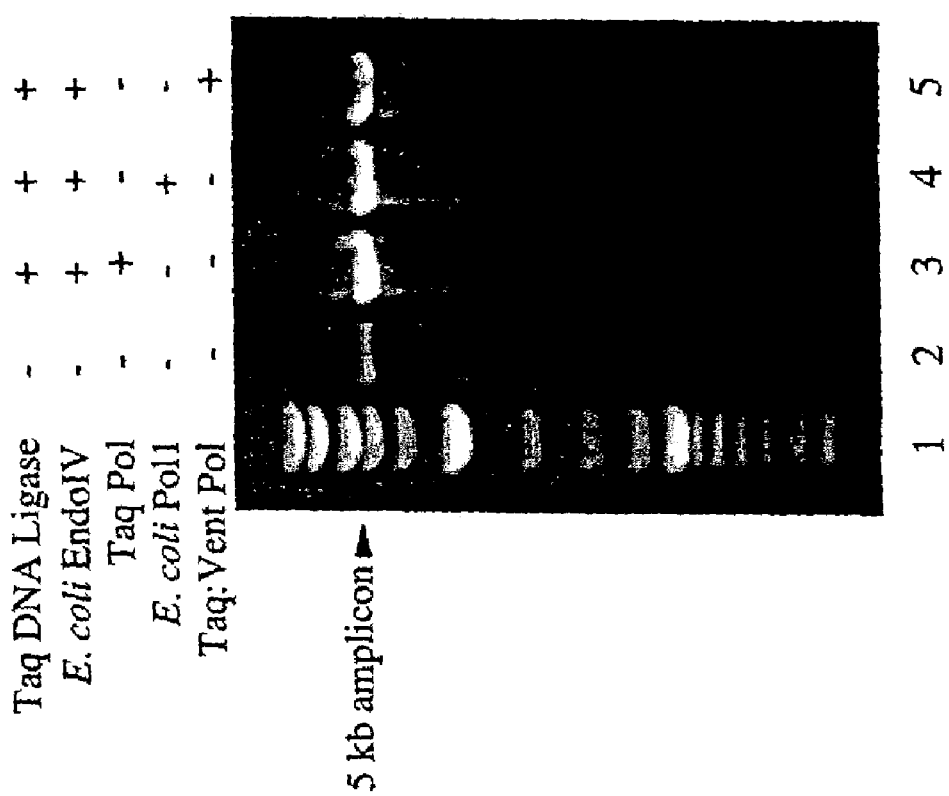

Example 2 and FIGS. 2A-2B show the negative effect on amplification yields of another type of DNA damage—depurination, which is induced in the presence of heat and citrate. Moreover, the example shows that the effect of a mixture of enzymes on amplification of DNA is not dependent on a single type of polymerase but rather polymerases from multiple alternative sources can be used. For example, *E. coli* PolI can be substituted by Taq DNA polymerase or a mixture of Taq and Vent® DNA polymerases to produce enhanced yields.

Figure 3:
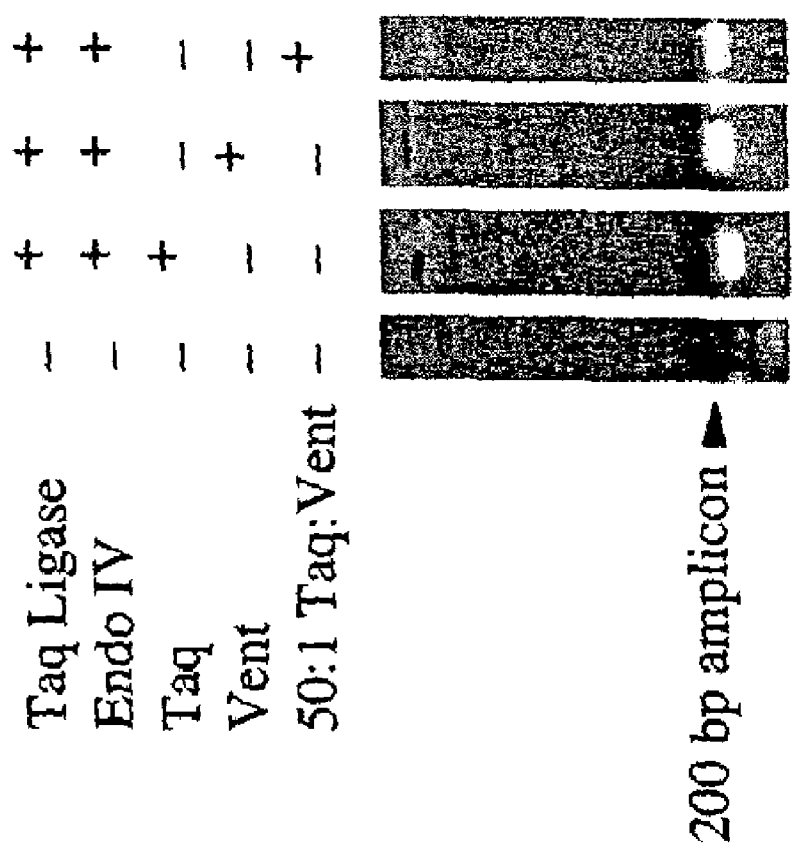

Example 3 and FIG. 3 show that the enhancement of amplification yields can be observed with short (200 bp) fragments. In fact, enhancement of amplification yields are observed for a wide range of sizes of DNA templates from as short as 100 bases to as long as 100 kb and it is believed that amplification yields for DNA even larger than 100 kb can be achieved. The upper limit of size is limited only by the polymerase in the amplification mixture.

FIG. 3 also shows that even when the DNA has been damaged through storage in a crude form (for example, within the cells of an organism that has itself been stored), amplification yields are significantly enhanced by the addition of a mixture of enzymes prior to amplification. Although the mixture of enzymes was added to template DNA prior to amplification, a similar yield effect can be seen when the template DNA is incubated with the mixture of enzymes that are thermostable equivalents during amplification or during a pre-amplification step.

Figure 4:
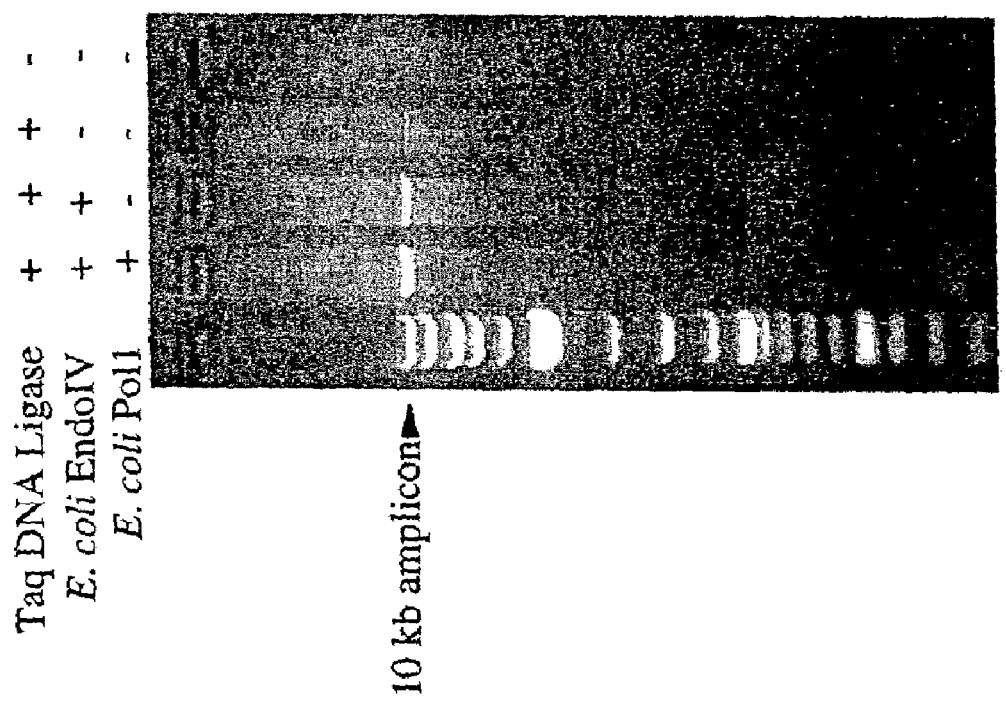

Example 4 and FIG. 4 show that ligase alone can enhance amplicon yield, but adding an AP endonuclease helps more. The best result was observed in this example when a ligase, an AP endonuclease, and a DNA polymerase were used prior to amplification. Furthermore, this example demonstrates that repair is not DNA size dependent. For example, similar results were obtained with 5 kb and 10 kb amplicons.

Figure 5:
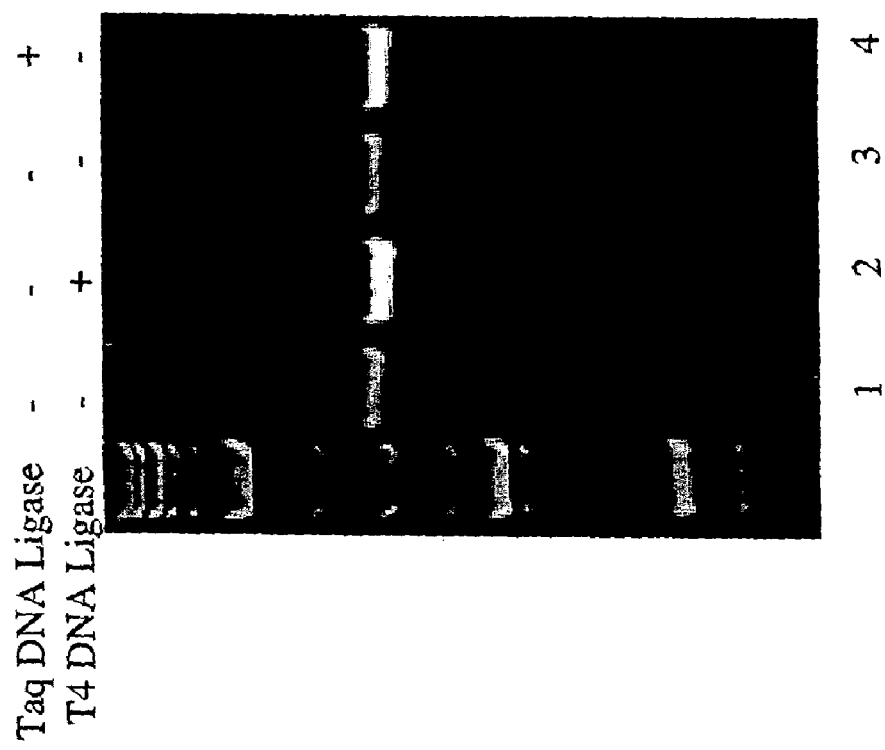

Example 5 and FIG. 5 show that an enhanced yield from amplification can be achieved using a ligase and that this effect can be achieved without limitation to a single source of ligase. FIG. 5 shows that Taq ligase and T4 ligase are both effective in enhancing amplification yield even when used without additional enzymes in a pre-incubation mix. This effect is also believed to occur if the ligase is added to the amplification mix (if thermostable). FIG. 5 also shows the benefit of this approach to amplifying environmental DNA obtained directly from soil samples that has been exposed in nature to a variety of damaging agents.

All references cited herein are incorporated by reference.

EXAMPLES

Example 1

Enhancing Amplification Yields for DNA with Various Extents of Damage

An assay was developed for optimizing the use of selected reagents to repair DNA prior to amplification.

Generation of Various Extents of Heat Damage

Various amounts of DNA damage were induced by heat treatment. This was achieved as follows: 100 μL lambda DNA (NEB#N3011, New England Biolabs, Inc., Ipswich, Mass.) at 0.5 mg/ml was aliquoted into separate tubes for heat treatment at 99° C. for 30 sec, 60 sec, 90 sec, 120 sec, and 180 sec, respectively in a PE2700 thermal cycler. A sample was used as a template for amplification without pretreatment.

The remaining damaged DNA was pretreated by the mixture of enzymes as follows: The damaged DNA templates were incubated at room temperature in the following mixture for 10 minutes:

DNA (5 ng, 2 ng and 1 ng);

100 μM dNTPs (NEB#M0447, New England Biolabs, Ipswich, Mass.);

1 mM NAD+(Sigma#N-7004, Sigma, St. Louis, Mo.);

80 units Taq ligase (NEB#M0208, New England Biolabs, Ipswich, Mass.) or 40-100 units of *E. coli* ligase;

0.1 units *E. coli* DNA polymerase I (*E. coli* pPolI) NEB#M0209, New England Biolabs, Inc., Ipswich, Mass.);

10 units *E. coli* Endo IV (NEB#M0304, New England Biolabs, Inc., Ipswich, Mass.) or 10 units of Tth Endo IV;

1× thermopol buffer (NEB#B9004, New England Biolabs, Inc., Ipswich, Mass.) to a final volume of 96 μL.

At the end of the reaction, the samples were transferred to ice and then amplified.

DNA Amplification Reaction

DNA amplification of lambda was performed using the following primers: CGAACGTCGCGCAGAGAAACAGG (L72-5R) (SEQ ID NO:1) and CCTGCTCTGCCGCT-TCACGC (L30350F) (SEQ ID NO:2) according to the method of Wang et al. *Nucl. Acids Res.* 32: 1197-1207(2004).

4 μl of amplification mixture was added to 96 μl of the above repair mixture. The amplification mixture contained 100 μM dNTPs, 5 units Taq DNA polymerase, 0.1 units Vent® (exo+) DNA polymerase, 5×10-7 M primer L72-5R and 5×10-7 M primer L30350F in 1× thermopol buffer.

To correct for any enzyme storage buffer effects, when a repair enzyme was omitted from a reactions the appropriate volume of its storage buffer was added to the reaction. In all cases, the amplification reactions were placed into a thermal cycler using the following parameters: 20 sec at 95° C. for 1 cycle followed by 5 sec at 94° C., then 5 min at 72° C. for 25 cycles. The size of the amplicon being amplified was 5 kb.

The results of amplification of DNA (5 kb) were determined by 1% agarose gel elecrophoresis. 6× loading dye (Molecular Cloning:A Laboratory Manual, $3^{rd}$ ed., eds. Sambrook and Russell, Cold Spring Harbor Press, Cold Spring Harbor, N.Y., 2001, pp. 5.4-5.17) was added to the 100 μl amplification reactions. 20 μl of this solution was then loaded onto the agarose gel along with 1 μg of 2-log ladder (NEB#N3200, New England Biolabs, Inc., Ipswich, Mass.) as a size standard.

Figure 1B:
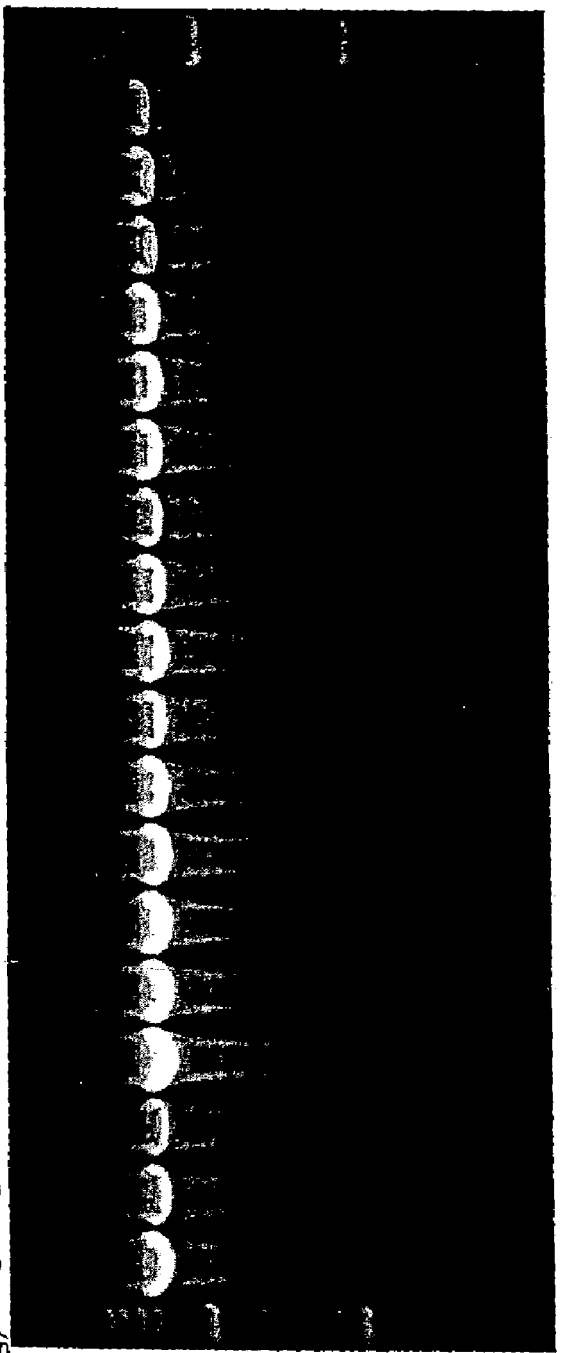
Figure 1C:
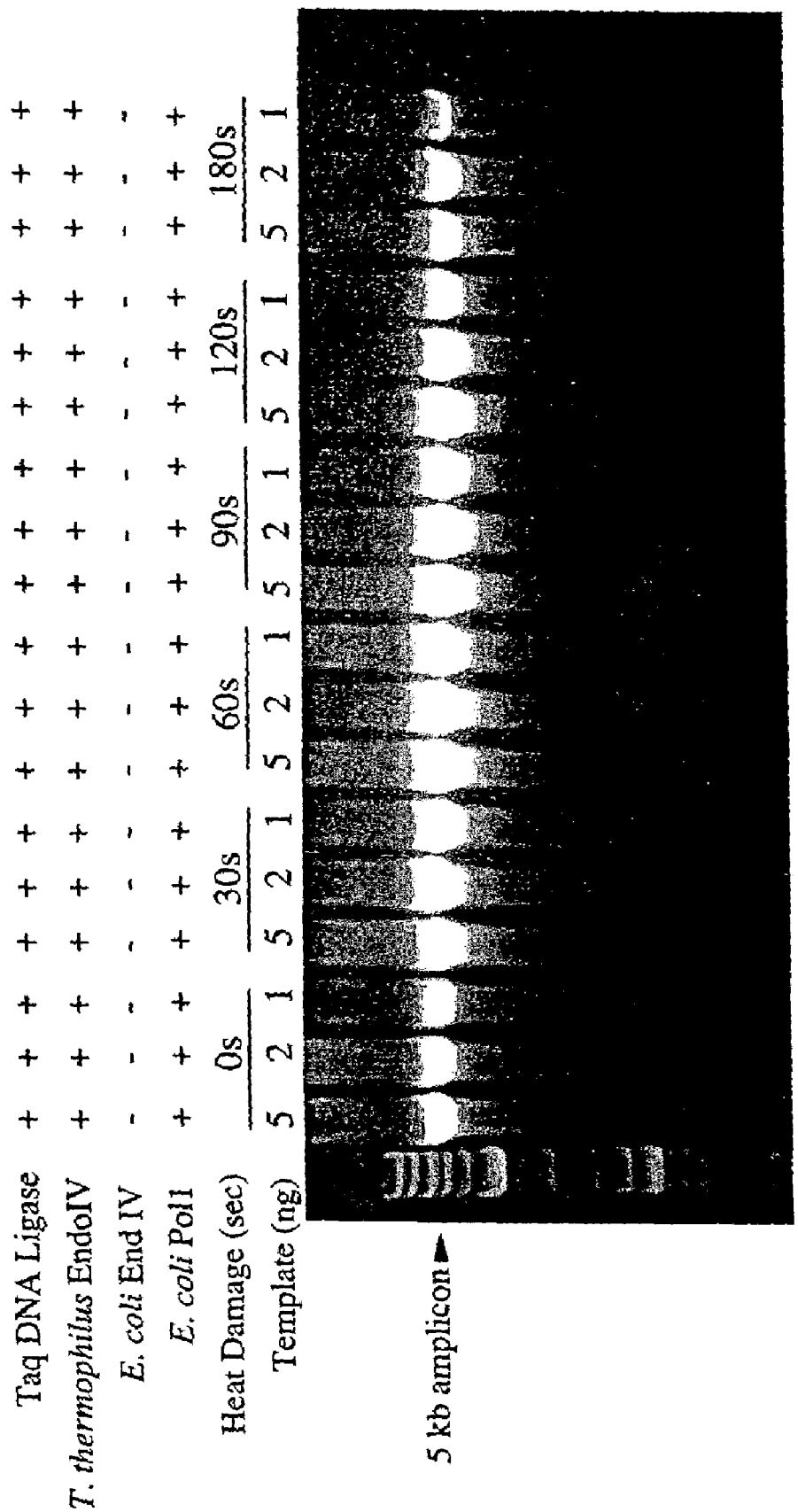
Figure 1D:
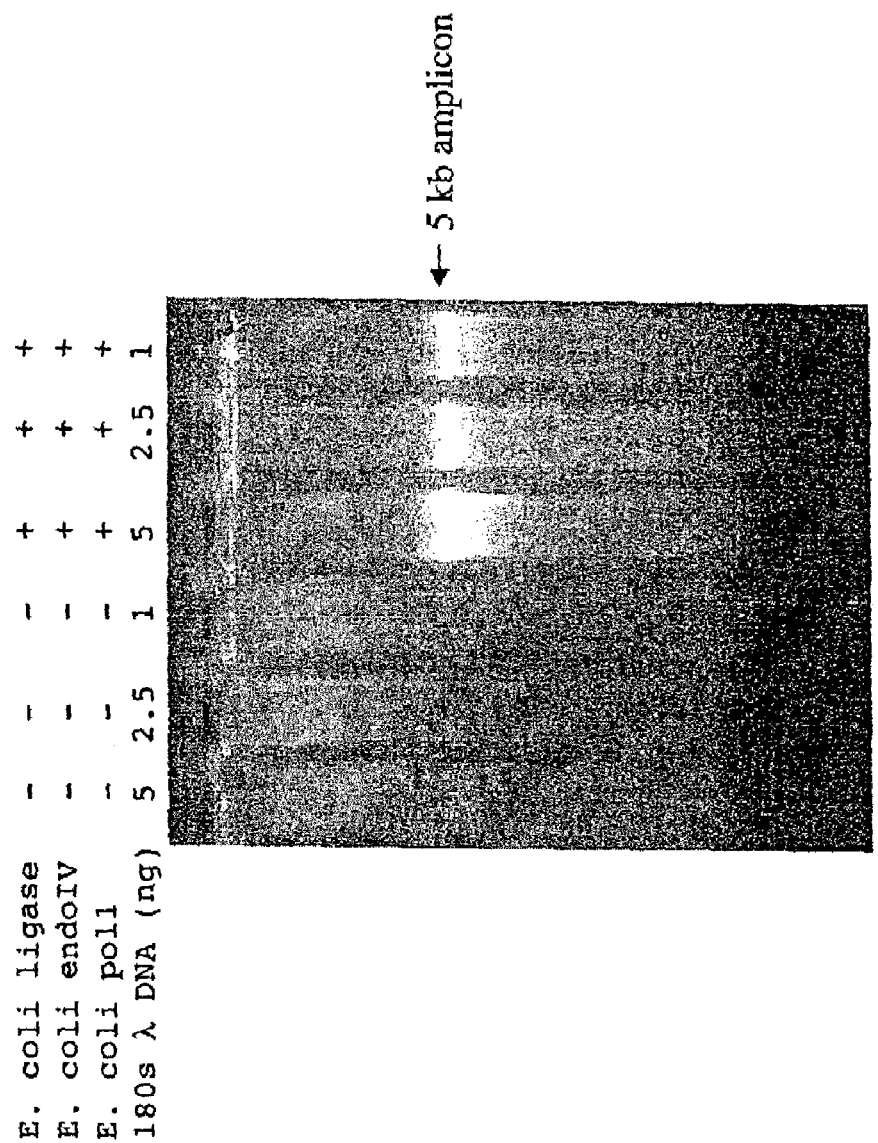

The amount of amplified DNA for each sample was compared by gel electrophoresis and the results are shown in FIG. 1A. When the samples were treated with a mixture of enzymes after heat treatment but prior to amplification, significant enhancement of amplification yields were achieved (FIGS. 1B, 1C and 1D).

Example 2

Increased Amplicon Yields from DNA with Induced Abasic Sites (after Citrate Treatment) Following Pretreatment with an Enzyme Mixture Generation of Various Extents of Damage Resulting from Abasic Site To assay the extent of repair of damaged DNA, various amounts of DNA damage was first induced by citrate treatment. This was achieved as follows:

DNA was depurinated as described by Ide, H., et al. *Biochemistry* 32(32):8276-83 (1993). Lambda DNA (NEB#N3011, New England Biolabs, Inc., Ipswich, Mass.) was ethanol precipitated. The DNA was resuspended in depurination buffer (100 mM NaCl, 10 mM citrate, pH 5.0) at a concentration of 0.5 mg/ml and incubated at 70° C. for 0, 20, 40, 80, 120, and 160 minutes. The sample was then ethanol precipitated and resuspended in EB buffer (Qiagen, Inc., Valencia, Calif.). The DNA concentration was determined by measuring the A260 of the DNA containing solutions.

Pretreatment of DNA with a Mixture of Enzymes

The damaged DNA was incubated at room temperature for 10 minutes in the following mixture:
DNA (2.5 ng/120 minute damage);
100 µM dNTPs;
1 mM NAD+;
80 units Taq ligase;
0.1 units Taq DNA polymerase or 0.1 units *E. coli* PolI (NEB#M0209, New England Biolabs, Inc., Ipswich, Mass.)) or 0.1 units Taq:0.002 units of Vent® Pol, (NEB#M0254, New England Biolabs, Inc., Ipswich, Mass.));
10 units *E. coli* Endo IV;
1× thermopol buffer to a final volume of 96 µl.

The above mixture was incubated at room temperature for 10 minutes and then transferred to ice prior to amplification.

DNA Amplification Reaction

Amplification was performed as described in Example 1 to generate a 5 kb amplicon. Amplicon yields were increased as compared with negative controls (FIG. 2A) by treating lambda DNA containing abasic sites with the mixture of enzymes. The results are shown in FIG. 2B for a series of pretreatments using different enzyme mixtures. The enzyme mixtures were varied with respect to the polymerase (*E. coli* PolI or Taq:Vent®).

Example 3

Improved Amplification Yield of DNA Extracted from an Intact Organism after Storage in a Preservative Genomic DNA was isolated from *Meganyctiphanes norvegica* (Krill) as described in Bucklin, A. & Allen, L. D. *Mol. Phylogenet. Evol.* 30(3):879-882 (2004). The Krill had been stored in ethanol since 1999.

Pretreatment of the Krill DNA by a mixture of enzymes was carried out as follows:
50 ng of *M. norvegica* genomic DNA;
100 µM dNTPs;
1 mM NAD+;
40 units of Taq ligase;
0.5 units Taq DNA polymerase, 0.2 units Vent® (exo+) DNA polymerase, or a Taq:Vent® (exo+) mix containing 0.05 units of Taq DNA polymerase and 0.001 units of Vent® (exo+);
10 units *E. coli* Endo IV;
1× Thermopol buffer to a final volume of 96 µl.

This reaction was incubated 15 minutes at room temperature before proceeding to the amplification step.

DNA Amplification Reaction

The amplification primers corresponded to 52F and 233R as described in Bucklin, A. & Allen, L. D. *Mol. Phylogenet. Evol.* 30(3):879-82 (2004) generating a 200 bp amplicon.

```
52F:    TTTTTAGCAATACACTACACAGCAA    (SEQ ID NO:3)

233R:   ATTACGCCAATCGATCACG          (SEQ ID NO:4)
```

Primers were added to a final concentration of 0.5 µM, and each dNTP to a final concentration of 200 µM. 1 µl of the 50:1 Taq:Vent® mix (5 units Taq DNA polymerase and 0.1 units Vent® (exo+) DNA polymerase added to the reaction) was then added to each reaction to a final volume of 100 µL.

For the control reaction (Lane 1), no Endo IV, Taq ligase or pretreatment polymerase was added. Volumes were adjusted accordingly. In reactions in which repair enzymes were omitted, the appropriate volume of enzyme storage buffer was added to control for buffer effects.

Cycling conditions were as follows: 30 sec at 94° C., 30 sec at 52° C. and 1 min 40 sec at 72° C. for 40 cycles. 25 µL (one quarter of the reaction) was loaded on a 1% agarose gel, prepared, electrophoresed and visualized as described above.

Increased amplicon yield from krill genomic DNA was observed after preincubation of the samples using the enzyme mixtures described above (FIG. 3).

Example 4

Increased Yields of 10 kb Amplicon Using Heat-Damaged DNA

Heat-damaged DNA was prepared as described in Example 1.

Lambda DNA was heated to 99° C. for 180 sec.

Pretreatment of damaged DNA by a mixture of enzymes was carried out as follows:
Lambda DNA (1 µg of 180 sec heat-treated DNA);
100 µM dNTPs;
1 mM NAD+;
80 units of Taq ligase;
0.1 unit of *E. coli* PolI;
100 units of *E. coli* Endo IV;
1× thermopol buffer to a volume of 96 µL.

The mixture was incubated for 10 minutes prior to amplification.

DNA amplification was performed as described in Example 1 except where specified below. Primers were added to the above 96 µl of preincubation mixture. Primer L71-10R (sequence GCACAGAAGCTATTATGCGTCCCCAGG) (SEQ ID NO:5) replaced L72-5R in Example 1. The icycler thermal cycler program was: 20 sec at 95° C. for 1 cycle, 5 sec at 95° C., 10 min at 72° C. for 25 cycles and then 10 min at 72° C. for 1 cycle. Amplicon size was 10 kb.

The DNA was visualized as described in Example 1 with the following exceptions. 20 µl of 6× loading buffer was added to the 100 µl amplification reaction. 10 µl of this solution was diluted to 100 µl with H₂O and 1× loading buffer. 20 µl of this was loaded into each lane. The gel was a 0.8% agarose gel. The results are shown in FIG. 4.

Example 5

Improved Amplification Yield of DNA Extracted from Soil Samples

Environmental DNA was isolated from the soil using an UltraClean Soil DNA Kit from MoBio Laboratories, Inc., Carlsbad, Calif. (catalog # 12800-50).

Pretreatment of DNA with a Ligase

A final volume of 100 µl containing 0.6 µg of environmental DNA isolated from soil and one of the two ligases described below in (a) and (b) formed the reaction mixture. This reaction mixture was then incubated at room temperature for 15 min.

(a) 1× Taq ligase buffer (New England Biolabs, Inc., Ipswich, Mass.) and 80 units of Taq ligase.

(b) 1× T4 ligase buffer (New England Biolabs, Inc., Ipswich, Mass.) and 800 units of T4 ligase (NEB#M0202, New England Biolabs, Inc., Ipswich, Mass.).

1 µl of reaction mixture was used in the amplification reaction described below.

DNA Amplification Reaction

DNA amplification was performed using primers: GGGGGXAGAGTTTGATCMTGGCTCA (SEQ ID NO:6) and GGGGGXTACGGYTACCTTGTTACGACTT (SEQ ID NO:7) (M=C or A, Y=C or T, X=8-oxo-Guanine). These primers target 16S rDNA having an amplicon size of 1.6 Kb.

The 50 µl reaction contained 10 pmol of each of the primers, 1 µl of the repaired environmental DNA, 200 µM dNTPs, 1× thermopol buffer, and 1.25 units Taq DNA polymerase. The amplification was performed using the following cycling parameters: 5 min at 94° C. for 1 cycle, 30 sec at 94° C., 1 min at 55° C., 1 min 40 sec at 72° C. for 32 cycles, then 5 min at 72° C. for 1 cycle.

Gel electrophoresis was performed as described in Example 1. The results are shown in FIG. 5.

Example 6

Improved Amplification Yield of Ultraviolet Light-Damaged DNA

To determine conditions for assaying the effectiveness of DNA repair, 50 µg lambda DNA (NEB#N3011, New England Biolabs, Inc., Ipswich, Mass.) was diluted in TE buffer (10 mM Tris-HCl, 1 mM EDTA, pH 7.5) to a concentration of 50 µg/ml and irradiated with 36 $J/m^2$ UV light for 0, 10, 20, 30, 40 and 50 sec.

Pretreatment of damaged DNA by a mixture of enzymes was carried out as follows:

The damaged DNA was incubated at room temperature for 15 minutes in the following mixture:

DNA (50 ng of lambda DNA-damaged for 0, 10, 20, 30, 40, or 50 seconds);
200 µM dNTPs;
1 mM $NAD^+$;
400 units Taq ligase;
0.1 units *E. coli* DNA polymerase I;
10 units *E. coli* Endo IV;
80 units or 10 units T4 pdg (also referred to as T4 Endo V). (Trevigen, Gaithersburg, Md.);
Thermopol buffer to a volume of 50 µl.

After the 15 minutes incubation, the 50 µl reaction mixture was added to 50 µl of an amplification solution. The amplification solution consisted of 40 pmol of each primer (L72-5R and L30350F as described in Example 1 or L72-2R (the DNA sequence was CCATGATTCAGTGTGCCCGTCTGG)(SEQ ID NO:8), 1× Thermopol buffer, 1 mM $NAD^+$, 200 µM dNTPs, 2.5 units Taq DNA polymerase (NEB#M0267, New England Biolabs, Inc., Ipswich, Mass.), and $H_2O$ to a final volume of 50 µL. Combining the 50 µL repair reaction with the 50 µl amplification solution gave a final volume of 100 µl.

The 100 µl solutions were placed into a thermal cycler. For the L72-5R and L30350F primer combination:

5 min at 94° C. for 1 cycle; 30 sec at 94° C., 60 sec at 58° C., and 4 min at 72° C. for 30 cycles; 5 min at 72° C. for 1 cycle.

For the L72-2R and L30350F primer combination:

5 min at 94° C. for 1 cycle; 30 sec at 94° C., 60 sec at 58° C., and 2 min at 72° C. for 30 cycles; 5 min at 72° C. for 1 cycle.

Figure 8:
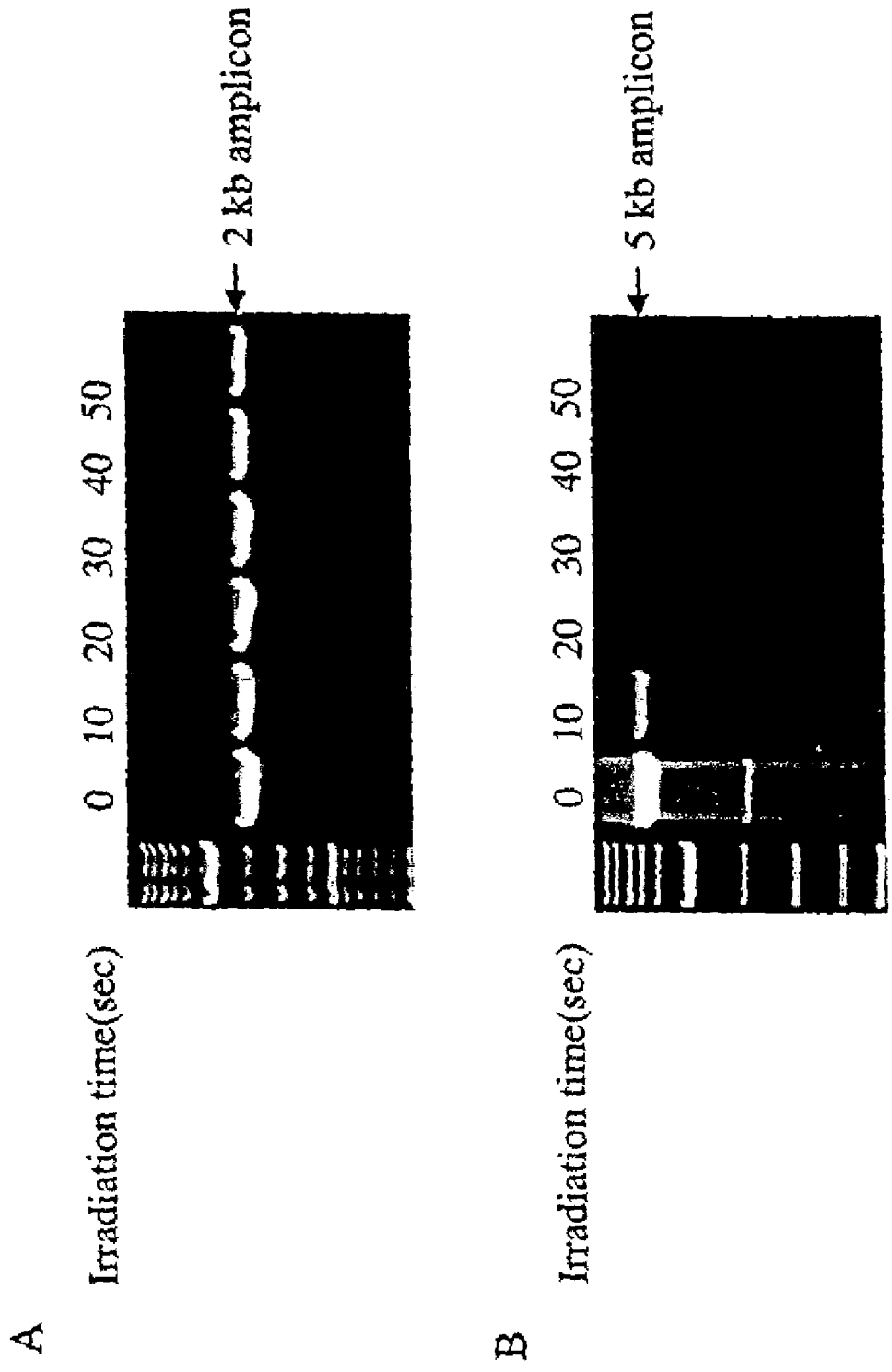
Figure 8:
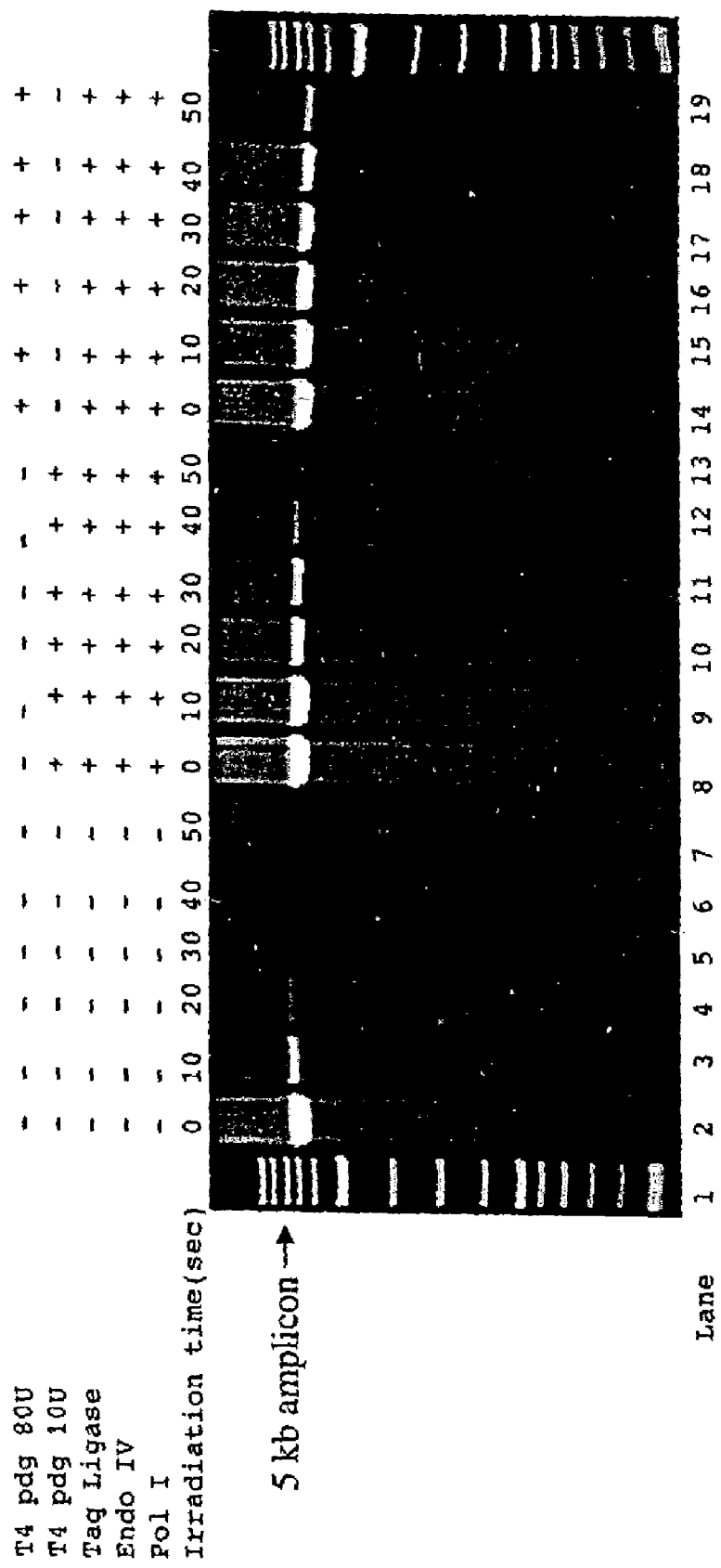

The presence of amplification product was visualized on a 1.8% agarose gel using ethidium bromide. The size of any band was compared against a lane containing the 2-log ladder (NEB#N3200S, New England Biolabs, Inc., Ipswich, Mass.) size standards. The results are shown in FIG. 8.

Example 7

Improved Amplification Yield of DNA Using the Nucleotide Excision Repair Proteins, UvrA, UvrB and UvrC Increased amplicon yield from krill genomic DNA is determined after preincubation of the samples using an enzyme mixture containing proteins involved in nucleotide excision repair.

Pretreatment of stored DNA by a mixture of enzymes is carried out as follows:

Stored DNA is incubated for 1-180 minutes at 4-37° C. in the following mixture:

DNA: 50 ng of *M. norvegica* genomic DNA;
100 µM dNTPs;
1 mM ATP;
400 units of Taq ligase;
0.1 units *E. coli* DNA polymerase I;
10 nM *E. coli* UvrA, 250 nM *E. coli* UvrB (or mutant UvrB*), plus or minus 50 nM *E. coli* UvrC
1× Thermopol buffer to a final volume of 96 µl.

* for mutant UvrB, see Zou, Y., et al. *Biochemistry* 43:4196-4205 (2004).

DNA amplification reactions are conducted as described in Example 3.

Example 8

Increasing Sequence Accuracy of a DNA Amplification Reaction by enzyme Cleavage of Heteroduplexes Experimental Conditions A. Adding Taq ligase to T7 Endo I was demonstrated to increase the T7 Endo I:DNA ration in a reaction mixture without randomly degrading the DNA. This approach makes it possible to reduce unwanted heteroduplexes resulting from mismatches in an amplification reaction.

The assay relies on treating a supercoiled DNA containing a cruciform structure with increasing amounts of T7 Endo I. 0, 1.6, 3.1, 6.2, 12.5, 25, 50, 100, 200, or 400 units of T7 Endo I (NEB#M0302, New England Biolabs, Inc., Ipswich, Mass.) was added to 50 µl reactions composed of 1 µg of pUC(AT)(Guan, C., et. al. *Biochemistry* 43:4313-4322 (2004)) and 1× NEBuffer 2 (NEB#B7002S, New England Biolabs, Inc., Ipswich, Mass.). Plasmid pAT25tetA can be used in place of pUC(AT)(Parkinson, M. J. & Lilley, D. M. *J. Mol. Biol.* 270:169-178 (1997)) and Bowater, R. P., et. al. *Biochemistry* 33:9266-9275 (1994)). Another set of reactions were set up simultaneously and used the same components as described above with the addition of 1 mM $NAD^+$ (Sigma catalog#N-7004, Sigma, St. Louis, Mo.) and 100 units of Taq ligase (using a stock of NEB#M0208 at a concentration of 100 u/µl). All reactions were incubated at 37° C. for 60 minutes.

The results were analyzed by running the reactions on a 0.9% TBE agarose gel, stained with ethidium bromide, and visualized using UV light (see FIG. 9). With no T7 Endo I present the pUC(AT) plasmid produced 2 bands on the gel corresponding to the supercoiled form (lower band) and the relaxed circular form (upper band).

T7 Endo I resolved the supercoiled pUC(AT) into the relaxed circular form and a linear form that ran intermediate to the supercoiled and relaxed circular forms. At certain T7 Endo I:DNA ratios, a smear was produced indicating that the T7 Endo I had degraded the DNA by non-specific enzymatic activity. The presence of Taq ligase significantly increased the usable T7 Endo I to DNA ratio. This ratio is further improved by substituting T7 Endo I with the mutant T7 Endo I described in International Publication No. WO 2005/052124.

B. Experimental conditions for determining the effectiveness of the T7 Endo I and ligase mix for removing heteroduplexes from PCR reactions.

Isolation of DNA from soil and amplification of the purified DNA is performed as described in Example 5 with the optional addition of 5 units T7 Endo I or mutant thereof. When T7 Endo 1 or mutant thereof is added, an additional amplification cycle is added (37° C. for 15 minutes for 1 cycle). The last step is to allow the AP endonuclease to cleave any heteroduplexes formed.

Gel electrophoresis is performed as described in Example 1. Heteroduplex DNA is visualized on the gel as described in Lowell, J. L. & Klein, D. A. *Biotechniques* 28:676-681 (2000)). Absence of heteroduplex DNA in the presence of T7 Endo I or mutant thereof shows the effectiveness of T7 Endo I or mutant thereof with ligase.

Unit definitions are described with the product description for each of the enzymes recited herein in the NEB catalog, New England Biolabs, Inc., Ipswich, Mass. For example, unit definition for T7 Endo I or mutant thereof is the amount of enzyme required to convert greater than 90% of 1 µg of supercoiled plasmid into greater than 90% linear DNA in a reaction volume of 50 µl in 1 hour at 37° C.

The T7 Endo I:DNA ratio can be increased without increasing non-specific cleavage of DNA in the presence of ligase.

Example 9

Increasing the Sequence Accuracy of a DNA Amplication Reaction after Oxidative Damage Generating DNA with Oxidative Damage The DNA subject to oxidative damage was pWB407 (Kermekchiev, M. B. et al. *Nucl. Acids Res.* 31:6139-47 (2003)). The damage was incurred using a combination of methylene blue (MB) and visible light as described previously (Sattler, et al. *Arch. Biochem Biophys.* 376(1):26-3 (2000)). Plasmid DNA (200 µg/ml in distilled water) was spotted on parafilm stretches (50 µl drops). MB was added to the drops to a final concentration ranging from 0 to 50 (0, 3, 6, 12.5, 25 and 50) µg/ml (100 µl final volume). Plates with these parafilm stretches were placed on ice and illuminated for 8 min. with a 1×100-W lamp. The MB-light-treated DNA was precipitated, dried, and then resuspended in 50 µl of TE buffer (pH 8.0). Final DNA concentration was determined by the absorbance of light at 260 nm.

DNA Amplification Conditions

A portion of pWB407 that contained the lacZ gene was amplified using primers 316-138, TGTCGATCAGGATGATCTGGACGAAGAGC (SEQ ID NO:9), and 316-137, CGAAAGCTTTCAAGGATCTTACCGCTGTTGAGA (SEQ ID NO:10). Primers 316-138 and 316-137 were based on the previously-described primers Kfd-29 and H₃Bla34, respectively (Kermekchiev, M. B. et al. *Nucl. Acids Res.* 31:6139-47 (2003)). The 100 µL PCR reactions contained either 10 or 50 ng of template DNA, indicated where appropriate, and 40 picomoles of each primer. The cycling conditions utilized varied with the thermal stable polymerase used for amplification.

Cycling conditions when using Taq DNA polymerase (NEB cat#M0267S, New England Biolabs, Inc., Ipswich, Mass.) had an initial denaturation step of 5 min at 94° C. for 1 cycle, then 30 sec at 94° C., 60 sec at 58° C., and 3 min 30 sec at 72° C. for 30 cycles, and finally 5 min at 72° C.

Cycling conditions when using Phusion DNA polymerase (NEB cat#F-530S, New England Biolabs, Inc., Ipswich, Mass.) had an initial denaturation step of 30 sec at 98° C. for 1 cycle, then 10 sec at 98° C., 30 sec at 62° C., and 1 min 30 sec at 72° C. for 30 cycles, and finally 5 min at 72° C.

The reaction outcomes were analyzed by loading 25 µL of the reaction on a 1.6% agarose gel, prepared, electrophoresed and visualized as described above. The marker used was the 2-log DNA ladder (NEB cat#N3200S, New England Biolabs, Inc., Ipswich, Mass.).

Amplification Accuracy Determination

The accuracy of DNA amplification from the pWB407 template was determined as described by Barnes, et al. *Gene* 112:29-35 (1992) and Kermekchiev, et al. *Nucl. Acids Res.* 31:6139-47 (2003). Amplicons containing the lacZ gene were generated from plasmids pWB407 that had been subjected to differing amounts of oxidative damage. The oxidative damage was performed using methylene blue as described above. The PCR reactions were performed using 50 ng of template as described above. After cycling, 10 units of the restriction endonuclease DpnI was added to each 100 µL PCR reaction and incubated for 2 hours at 37° C. This step eliminated the original template plasmid. Next, the resulting amplification products were extracted with phenol/chloroform precipitation using isopropanol (Molecular Cloning: A Laboratory Manual, 3$^{rd}$ ed., eds. Sambrook and Russell, Cold Spring Harbor Press, Cold Spring Harbor, N.Y., 2001, pp. 6.25, A8.12-A8.24). Precipitated products were resuspended in $H_2O$ and cut with the restriction endonucleases StyI and HindIII using conditions recommended by the manufacturer (New England Biolabs, Inc., Ipswich, Mass.). The DNA digestion reactions were stopped by inactivating the HindIII and StyI enzymes by heating to 65° C. for 20 min. The restriction digestion products were purified using a microcon YM-100 column (Millipore, Billerica, Mass.) to eliminate short DNA fragments.

The repair reaction mixtures in a total of 50 µl contained 10 or 50 ng of pWB407 amplicons+/− methylene blue incubation. The repair reactions contained 20 mM Tris-HCl (pH 8.8 at 25° C.), 10 mM KCl, 10 mM $(NH_4)_2SO_4$, 2 mM $MgSO_4$, 0.1% Triton X-100, 1 mM $NAD^+$, 200 µM dNTPs (dATP, dTTP, dCTP, and dGTP), and various repair enzyme mixtures.

The repair enzyme mixtures used separately or in various combinations in a total volume of 50 ul were:

0.4 units Fpg, NEB cat#M0240S, New England Biolabs, Inc., Ipswich, Mass.);

200 units Taq ligase;

0.1 units *E. coli* DNA polymerase I;

10 units *E. coli* Endo IV;

1 mM NAD+;

100 µM dNTPs;

1× Thermopol buffer.

The reactions were incubated at 25° C. for 15 minutes. After the incubation, 50 µL of a PCR mix (20 mM Tris-HCl (pH 8.8 at 25° C.), 10 mM KCl, 10 mM $(NH_4)_2SO_4$, 2 mM $MgSO_4$, 0.1% Triton X-100, 1 mM $NAD^+$, 200 µM dNTPs (dATP, dTTP, dCTP, and dGTP), 2.5 units Taq DNA polymerase (NEB cat#M0267S, New England Biolabs, Inc., Ipswich, Mass.) was added to the 50 µL repair reaction and this new solution was subjected to thermal cycling conditions for PCR. The amplicons from these reactions were purified and restriction enzyme digested as described for other amplicons above.

The amplicons were cloned into the pWB407 plasmid. Plasmid pWB407 was prepared by digestion with the restriction endonucleases StyI and HindIII followed by a 30-minute incubation at 37° C. with 1 unit/μg DNA of antarctic phosphatase (NEB cat#M0289S, New England Biolabs, Inc., Ipswich, Mass.). The dephosphorylated pWB407 vector backbone was purified by agarose gel electrophoresis. Gel extraction was performed with a QIAquick Gel Extraction Kit (Qiagen, Valencia, Calif.).

The digested amplicons were ligated into the prepared pWB407 plasmids in 30 μL reactions using approximately 0.1 μg vector DNA and about 0.5 μg amplicon. T4 ligase was used to perform the ligation following the manufacturers recommended conditions (New England Biolabs, Inc., Beverly, Mass.). Ligation products were electroporated into *E. coli* strain WB441 (Barnes, W. *Gene* 112:29-35 (1992)). The selective indicator plates used were LB plates containing 50 μg/ml ampicilin and 80 ug/ml Xgal. Before plating, the bacteria were incubated in rich broth for 1 hour at 37° C. to allow expression of the ampicilin resistance.

Control transformations lacking ligase treatment resulted in zero colonies. Colonies were scored for blue color after one day at 37° C., and one or two days at 25° C. The results are shown in FIGS. 10 and 11.

Example 10

Increasing the Sequence Accuracy of a DNA Amplification Reaction After Deamination Damage Generating Deaminated DNA The DNA subject to deamination was pWB407 (Kermekchiev, et al. Nucleic Acids Research, 2003, Vol. 31, 6139-6147). The damage was incurred using random mutagenesis with nitrous acid as described in Yan, W. et al. J Virol. 2003 February;77(4):2640-50. Nitrous acid can deaminate guanine in DNA to xanthine, cytosine to uracil, and adenine to hypoxanthine.

Plasmid DNA (2 mg) was treated with 0.7 M $NaNO_2$ in 1M acetate buffer, pH 4.6. The reaction was terminated at various time points by addition of 4 volumes of ice-cold 1 M Tris-Cl (pH 7.9. The plasmid DNA was precipitated, dried and then resuspended in 100 ml of TE buffer.

Pretreatment Reaction to Repair Deaminated Bases

The repair enzyme mixtures used separately or in various combinations in total volume of 50 ml were:

(a)
1 unit Human Aag, New England Biolabs, Inc., Ipswich, Mass.;
2 units Endo III (NEB cat # M0268S), New England Biolabs, Inc., Ipswich, Mass.;
2 units Endo V (NEB cat # M0305S), New England Biolabs, Inc., Ipswich, Mass.;
2 units UDG (NEB cat # M0280S), New England Biolabs, Inc., Ipswich, Mass.;
200 units *E. coli* Endo IV;
0.1 units *E. coli* DNA polymerase I;
10 units *E. coli* Endo IV;
1 mM NAD+;
100 mM dNTPs;
1× Thermopol buffer.

(b)
2 units Endo V (NEB cat # M0305S), New England Biolabs, Inc., Ipswich, Mass.;
2 units UDG (NEB cat # M0280S), New England Biolabs, Inc., Ipswich, Mass.;
200 units *E. coli* Endo IV;
0.1 units *E. coli* DNA polymerase I;
10 units *E. coli* Endo IV;
1 mM NAD+;
100 mM dNTPs;
1× Thermopol buffer.

(c)
2 units Endo V (NEB cat # M0305S), New England Biolabs, Inc., Ipswich, Mass.;
200 units *E. coli* Endo IV;
0.1 units *E. coli* DNA polymerase I;
10 units *E. coli* Endo IV;
1 mM NAD+;
100 mM dNTPs;
1× Thermopol buffer.

(d)
1 unit Human Aag, New England Biolabs, Inc., Ipswich, Mass.;
2 units Endo III (NEB cat # M0268S), New England Biolabs, Inc., Ipswich, Mass.;
200 units *E. coli* Endo IV;
0.1 units *E. coli* DNA polymerase I;
10 units *E. coli* Endo IV;
1 mM NAD+;
100 mM dNTPs;
1× Thermopol buffer.

(e)
1 unit Human Aag, New England Biolabs, Inc., Ipswich, Mass.;
2 units UDG (NEB cat # M0280S), New England Biolabs, Inc., Ipswich, Mass.;
200 units *E. coli* Endo IV;
0.1 units *E. coli* DNA polymerase I;
10 units *E. coli* Endo IV;
1 mM NAD+;
100 mM dNTPs;
1× Thermopol buffer.

(f)
1 unit Human Aag, New England Biolabs, Inc., Ipswich, Mass.;
2 units Endo V (NEB cat # M0305S), New England Biolabs, Inc., Ipswich, Mass.;
200 units *E. coli* Endo IV;
0.1 unit *E. coli* DNA polymerase I;
10 units *E. coli* Endo IV;
1 mM NAD+;
100 mM dNTPs;
1× Thermopol buffer.

The amplification reaction conditions and amplification accuracy determination are performed as described in Example 9.

Example 11

Unit Definitions

Thermophilic Ligase Unit

One unit is defined as the amount of enzyme required to give 50% ligation of 1 μg of BstE II-digested lambda DNA in a total reaction volume of 50 μl in 15 minutes at 45° C.

Mesophilic Ligase Unit

One unit is defined as the amount of enzyme required to give 50% ligation of Hind III digested lambda DNA (5' DNA termini concentration of 0.12 µM, 300 µg/ml) in a total reaction volume of 20 µl in 30 minutes at 16° C.

AP Endonuclease Unit

One unit is defined as the amount of enzyme required to cleave 1 pmol of a 34-mer oligonucleotide duplex containing a single AP site in a total reaction volume of 10 µl in 1 hour at 37° C.

Mesophilic Polymerase Unit

One unit is defined as the amount of enzyme that will incorporate 10 nmol of dNTP into acid-insoluble material in a total reaction volume of 50 µl in 30 minutes at 37° C. with 33 µM dNTPs including [3H]-dTTP and 70 µg/ml denatured herring sperm DNA.

Thermophilic PolymeraseuUnit

One unit is defined as the amount of enzyme that will incorporate 10 nmol of dNTP into acid-insoluble material in a total reaction volume of 50 µl in 30 minutes at 75° C. with 200 µM dNTPs including [3H]-dTTP and 200 µg/ml activated Calf Thymus DNA.

For unit definitions for UDG and Fpg, (see NEB catalog, New England Biolabs, Inc., Ipswich, Mass.).

| Gene Name | Activity | Accession Number |
|---|---|---|
| UNG | Uracil-DNA glycosylase | NM_080911 |
| SMUG1 | Uracil-DNA glycosylase | NM_014311 |
| MBD4 | Removes U or T opposite G at CpG sequences | NM_003925 |
| TDG | Removes U, T or ethenoC opposite G | NM_003211 |
| OGG1 | Removes 8-oxoG opposite C | NM_016821 |
| MUTYH (MYH) | Removes A opposite 8-oxoG | NM_012222 |
| NTHL1 (NTH1) | Removes Ring-saturated or fragmented pyrimidines | NM_002528 |
| MPG | Removes 3-meA, ethenoA, hypoxanthine | NM_002434 |
| NEIL1 | Removes thymine glycol | NM_024608 |
| NEIL2 | Removes oxidative products of pyrimidines | NM_145043 |
| XPC | Binds damaged DNA as complex | NM_004628 |
| RAD23B (HR23B) | XPC, RAD23B, CETN2 | NM_002874 |
| CETN2 | | NM_004344 |
| RAD23A (HR23A) | Substitutes for HR23B | NM_005053 |
| XPA | Binds damaged DNA in preincision complex | NM_000380 |
| RPA1 | Binds DNA in preincision complex | NM_002945 |
| RPA2 | | NM_002946 |
| RPA3 | RPA1, RPA2, RPA3 | NM_002947 |
| ERCC5 (XPG) | 3' incision | NM_000123 |
| ERCC1 | 5' incision subunit | NM_001983 |
| ERCC4 (XPF) | 5' incision subunit | NM_005236 |
| LIG1 | DNA joining | NM_000234 |
| CKN1 (CSA) | Cockayne syndrome; Needed for transcription-coupled NER | NM_000082 |
| ERCC6 (CSB) | | NM_000124 |
| XAB2 (HCNP) | CKN1, ERCC6, XAB2 | NM_020196 |
| DDB1 | Complex defective in XP group E | NM_001923 |
| DDB2 | DDB1, DDB2 | NM_000107 |
| MMS19L (MMS19) | Transcription and NER | NM_022362 |
| FEN1 (DNase IV) | Flap endonuclease | NM_004111 |
| SPO11 | endonuclease | NM_012444 |
| FLJ35220 (ENDOV) | incision 3' of hypoxanthine and uracil | NM_173627 |
| FANCA | Involved in tolerance or repair of DNA crosslinks | NM_000135 |
| FANCB | | NM_152633 |
| FANCC | FANCA, FANCB, FANCC, FANCD2, FANCE, FANCF, FANCG, FANCL | NM_000136 |
| FANCD2 | | NM_033084 |
| FANCE | | NM_021922 |
| FANCF | | NM_022725 |
| FANCG (XRCC9) | | NM_004629 |
| FANCL | | NM_018062 |
| DCLRE1A (SNM1) | DNA crosslink repair | NM_014881 |
| DCLRE1B (SNM1B) | Related to SNM1 | NM_022836 |
| NEIL3 | Resembles NEIL1 and NEIL2 | NM_018248 |
| ATRIP (TREX1) | ATR-interacting protein 5' alternative ORF of the TREX1/ATRIP gene | NM_130384 |
| NTH | Removes damaged pyrimidines | NP_416150.1 |
| NEI | Removes damaged pyrimidines | NP_415242.1 |
| NFI | Deoxyinosine 3' endonuclease | NP_418426.1 |
| MUTM | Formamidopyrimidine DNA glycosylase | NP_418092.1 |
| UNG | Uracil-DNA glycosylase | NP_417075.1 |
| UVRA | DNA excision repair enzyme complex | NP_418482.1 |
| UVRB | | NP_415300.1 |
| UVRC | UVRA, UVRB, UVRC | NP_416423.3 |
| DENV | Pyrimidine dimer glycosylase | NP_049733.1 |

The invention claimed is:

1. A method for enhancing at least one of fidelity and yield of an amplification product of a damaged polynucleotide, comprising the steps of:
   (a) incubating the polynucleotide containing one or more damaged sites with a reaction mixture comprising an effective amount of ligase selected from Taq ligase or *E. coli* ligase in the presence of $NAD^+$, and in the absence of Endonuclease (Endo) VI, for repairing the damaged sites in the polynucleotide; and
   (b) adding amplification reagents to the reaction mixture so as to permit in vitro polymerase-dependent amplification of the polynucleotide in the reaction mixture.

2. A method according to claim 1, wherein step (a) is performed at a single temperature.

3. A method according to claim 1, wherein the damaged polynucleotide contains one or more damaged sites selected from apurinic/apyrimidinic (AP) bases, mutagenized nucleotides, modified nucleotides, nicks, gaps and DNA-DNA cross-links.

4. A method according to claim 1, wherein the polynucleotide is obtained from a natural source.

5. A method according to claim 1, wherein the polynucleotide is obtained from preserved biological material.

6. A method according to claim 1, wherein the polynucleotide is obtained from forensic evidence.

7. A method according to claim 1, wherein the polynucleotide is ancient.

8. A method according to claim 1, wherein the polynucleotide is obtained from a tissue biopsy.

9. A method according to claim 1, wherein the reaction mixture in step(a) further comprises a T7 Endo I or mutant thereof.

10. A method according to claim 1, wherein the reaction mixture in step (a) further comprises a polymerase and an AP endonuclease.

11. A method according to claim 10, wherein the AP endonuclease is a class II AP endonuclease.

12. A method according to claim 10, wherein the AP endonuclease is selected from the group consisting of a T4 endonuclease, an *E. coli* endonuclease, Tth Endo IV, and human AP endonuclease.

13. A method according to claim 10, wherein the AP endonuclease is *E. coli* Endo IV.

14. A method according to claim 10, wherein the polymerase is selected from the group consisting of Taq DNA polymerase, Bst DNA polymerase, T4 DNA polymerase, T7 DNA polymerase, *E. coli* DNA polymerase I and an archaeal DNA polymerase or modifications thereof.

15. A method according to claim 10, wherein the polymerase is an archaeal DNA polymerase and the archaeal polymerase is selected from Pfu, Vent®, Deep Vent®, 9° North, and GBD DNA polymerase.

16. A method according to claim 10, wherein the polynucleotide is DNA and the reaction mixture in step (a) comprises 1-100 units of the AP endonuclease, 0.05-0.25 units of the polymerase and 5-500 units of the ligase.

17. A method according to claim 10 or 16, wherein the reaction mixture in step (a) further comprises T4 pyrimidine dimer glycosylase (pdg).

18. A method according to claim 10 or 16, wherein the reaction mixture in step (a) further comprises [fapy]-DNA glycosylase (Fpg).

19. A method according to claim 10 or 16, wherein the reaction mixture in step (a) further comprises at least one of UvrA, UvrB, UvrC, UvrD and Cho.

20. A method according to claim 10 or 16, wherein the reaction mixture in step (a) further comprises at least one glycosylase/lyase selected from the group consisting of Endo III, Endo VIII, *E coli* Fpg, OGGI, and T4 pdg.

21. A method according to claim 10 or 16 or 20, wherein the reaction mixture in step (a) further comprises at least one glycosylase selected from the group consisting of UDG, AlkA and Aag.

22. A method according to claim 10 or 16, wherein the polymerase is a Bst DNA polymerase, the AP endonuclease is Endo IV, the ligase is Taq ligase, the reaction mixture in step (a) further comprising one or more glycosylases and one or more glycosylase/lyases.

23. A method according to claim 1, wherein the amplification is PCR amplification, helicase-dependent amplification, transcription-mediated amplification, strand-displacement amplification, rolling circle amplification or whole genome amplification.

24. A method according to claim 1, wherein the polynucleotide is a single-stranded RNA and the amplification is RT-amplification.

25. A method according to claim 1, wherein amplification of the polynucleotide is capable of producing an amplicon in a size range of 50 nucleotides to 100,000 nucleotides in a polymerase chain reaction.

26. A method according to claim 22, wherein the one or more glycosylases is UDG and the one or more glycosylase/lyases are Fpg, T4 pdg and Endo VIII.

27. A method according to claim 10, wherein the polymerase is an *E. coli* Y family DNA polymerase.

* * * * *

UNITED STATES PATENT AND TRADEMARK OFFICE
CERTIFICATE OF CORRECTION

| | | |
|---|---|---|
| PATENT NO. | : 7,700,283 B2 | Page 1 of 1 |
| APPLICATION NO. | : 11/255290 | |
| DATED | : April 20, 2010 | |
| INVENTOR(S) | : Evans et al. | |

It is certified that error appears in the above-identified patent and that said Letters Patent is hereby corrected as shown below:

Title page,

Item [75], Inventors,
Replace "Romaldas" with -- Romualdas --

Signed and Sealed this

Twenty-third Day of August, 2011

David J. Kappos
*Director of the United States Patent and Trademark Office*